(12) United States Patent
Almarsson et al.

(10) Patent No.: US 6,559,293 B1
(45) Date of Patent: May 6, 2003

(54) TOPIRAMATE SODIUM TRIHYDRATE

(75) Inventors: Örn Almarsson, Shrewsbury, MA (US); Jules Remenar, Framingham, MA (US); Matthew L. Peterson, Framingham, MA (US)

(73) Assignee: Transform Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 10/232,589

(22) Filed: Sep. 3, 2002

Related U.S. Application Data

(60) Provisional application No. 60/406,974, filed on Aug. 30, 2002, provisional application No. 60/380,288, filed on May 15, 2002, and provisional application No. 60/356,764, filed on Feb. 15, 2002.

(51) Int. Cl.⁷ .............................. C07H 5/04; C07H 5/06; C07H 1/00
(52) U.S. Cl. ...................................... 536/18.7; 536/1.11
(58) Field of Search .............................. 536/1.11, 18.7; 514/23, 454

(56) References Cited

U.S. PATENT DOCUMENTS

| | | | |
|---|---|---|---|
| 4,513,006 A | 4/1985 | Maryanoff et al. | 514/23 |
| 5,753,693 A | 5/1998 | Shank | 514/454 |
| 5,760,007 A | 6/1998 | Shank et al. | 514/23 |
| 5,935,933 A | 8/1999 | Shank et al. | 514/23 |
| 5,952,187 A * | 9/1999 | Stenglein et al. | |
| 5,998,380 A | 12/1999 | Ehrenberg et al. | 514/23 |
| 6,191,117 B1 | 2/2001 | Kozachuk | 514/454 |
| 6,201,010 B1 | 3/2001 | Cottrell | 514/454 |
| 6,319,903 B1 | 11/2001 | Carrazana et al. | 514/23 |

OTHER PUBLICATIONS

Physician's Desk Reference, 56$^{th}$ Ed., pp. 2590–2595 (2002).

* cited by examiner

Primary Examiner—James O. Wilson
Assistant Examiner—Traviss C. McIntosh
(74) Attorney, Agent, or Firm—Pennie & Edmonds LLP

(57) ABSTRACT

The invention encompasses novel salts of topiramate, and pharmaceutically acceptable polymorphs, solvates, hydrates, dehydrates, co-crystals, anhydrous, or amorphous forms thereof, as well as pharmaceutical compositions and pharmaceutical unit dosage forms containing the same. In particular, the invention encompasses pharmaceutically acceptable salts of topiramate, including without limitation topiramate sodium, topiramate lithium, topiramate potassium, or polymorphs, solvates, hydrates, dehydrates, co-crystals, anhydrous, and amorphous forms thereof. The invention further encompasses novel co-crystals or complexes of topiramate, as well as pharmaceutical compositions comprising them. The invention also encompasses methods of treating or preventing a variety of diseases and conditions including, but not limited to, seizures, epileptic conditions, tremors, cerebral function disorders, obesity, neuropathic pain, affective disorders, tobacco cessation, migraines, and cluster headache.

1 Claim, 13 Drawing Sheets

TOPIRAMATE SODIUM TRIHYDRATE

The application is related to U.S. provisional patent application Nos. 60/356,764 filed Feb. 15, 2002, No. 60/380,288 filed May 15, 2002, and 60/406,974 filed Aug. 30, 2002, all of which are incorporated herein by reference in their entireties.

1. FIELD OF INVENTION

This invention relates to compounds, pharmaceutical compositions, and methods for the treatment or prevention of seizures, epilepsy, tremors, affective disorders, obesity, neuropathic pain, and migraines.

2. BACKGROUND OF THE INVENTION

2.1. Topiramate

Topiramate is a sulfamate-substituted monosaccharide, which is chemically named 2,3:4,5-Di-O-isopropylidene-β-D-fructopyranose sulfamate. The molecular formula of topiramate is $C_{12}H_{21}NO_8S$, and its chemical structure is represented by formula I:

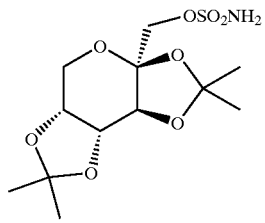

Topiramate is a white crystalline powder with a solubility in water of 9.8 mg/mL, and it is freely soluble in acetone, chloroform, dimethylsulfoxide, and ethanol. See, *Physician's Desk Reference*, 56$^{th}$ ed., pp. 2590–2595 (2002).

Topiramate is sold in the United States under the trade name TOPAMAX® (Ortho-McNeil Pharmaceutical, Inc., Raritan, N.J., U.S.A.). TOPAMAX® has been approved for use as an antiepileptic agent as an adjuvant therapy for patients with partial onset seizures, or primary generalized tonic-clonic seizures. See generally, *Physician's Desk Reference*, 56$^{th}$ ed., 2590–2595 (2002); see also, U.S. Pat. No. 4,513,006. Adverse effects associated with the administration of topiramate include, but are not limited to, somnolence, dizziness, ataxia, speech disorders and related speech problems, psychomotor slowing, abnormal vision, difficulty with memory, paresthesia, diplopia, renal calculi (kidney stones), hepatic failure, pancreatitis, renal tubular acidosis, acute myopia and secondary angle closure glaucoma. *Physician's Desk Reference*, 56$^{th}$ ed., pp. 2590–2595 (2002).

Topiramate has been investigated for use as anti-obesity agent, a blood pressure lowering agent, and a mood stabilizer, including use as an antimanic, antidepressant, and for the treatment of post-traumatic stress disorder, migraines, cluster headaches, and neuropathic pain. See, e.g., U.S. Pat Nos. 6,191,117; 6,201,010; 5,753,693; 5,998,380; 6,319,903; 5,935,933; and 5,760,007. However, the time it takes for topiramate to reach peak plasma levels (i.e., about two hours) may be too slow for its effective use in the treatment of some conditions, such as neuropathic pain. Moreover, the compound's relatively low aqueous solubility makes it difficult to provide in a controlled release dosage form, which may be necessary for the effective treatment of conditions such as obesity, and which may allow a reduction in adverse effects associated with peak plasma levels of the drug. Therefore, new highly soluble and bioavailable forms of topiramate are needed in order to increase the safety and effectiveness of the compound.

2.2. Epilepsy, Seizures, and Tremors

Epilepsy is a chronic disorder or condition characterized by recurring motor, sensory, or behavioral or psychic alterations or malfunctions that can include unconsciousness or convulsive movements. See Valente L R, *Clinician Reviews*, 10(3): 79 (2000). A variety of seizure types can occur, from partial seizures to generalized seizures.

There are three classifications of partial seizures: simple, complex, and secondarily generalized. A patient with a simple partial seizure (also called Jacksonian seizure) may experience jerking or shaking in one area of the body, which may progress to other areas. A simple partial seizure may also manifest with somatosensory, visual, auditory, olfactory, autonomic (sweating, pupillary dilation, epigastric rising), or psychic symptoms. With complex partial seizures, the patient's consciousness may be impaired, either immediately, or gradually over time after simple partial onset. Patients experiencing a complex partial seizure will often exhibit a blank stare followed by automatism, which may include lip smacking, chewing, picking at clothing, or purposeless walking. Finally, secondarily generalized seizures can evolve directly from simple partial or complex partial seizures, or progress from simple partial to complex partial to generalized. See, Leppik I E. *Contemporary Diagnosis and Management of the Patient With Epilepsy*. 4$^{th}$ Ed., Newtown, Pa.: Handbooks in Health Care Co (1999).

Generalized seizures can be convulsive or nonconvulsive, but always involve a loss of consciousness. Absence seizures (formerly called "petit mal") may be typical or atypical, and are strongly linked to genetic predisposition. Typical absence seizures may be precipitated by photic stimulation or hyperventilation. The symptoms include a blank stare, eye blinking, and in some instances automatisms, and the patient may experience increased or decreased tone. These brief seizures tend to occur in groups, and can occur 50 to 100 times in a day. See, Leppik I E. *Contemporary Diagnosis and Management of the Patient With Epilepsy*. 4$^{th}$ Ed., Newtown, Pa.: Handbooks in Health Care Co (1999). Atypical absence seizures, begin and end less abruptly the typical absence seizures, but last longer and result in more pronounced changes in tone.

Myoclonic seizures manifest with quick, involuntary muscle jerks lasting a few seconds. These muscle jerks or movements may be isolated to one body part or involve the entire body. Myoclonic seizures may accompany other generalized seizures and are common to specific epilepsy syndromes. Tonic seizures are generally associated with other epileptic syndromes, and typically last less than a minute. Tonic seizures involve violent spasm or stiffening, and in many instances, the lower extremities are extended and the upper extremities are flexed. In addition, the patient may turn the head or eyes to one side. Clonic seizures, most common in neonates and children, also exhibit repetitive muscular jerks but at a slower rate, and while clonic seizures can last as long as several minutes, brief episodes are more common. See, Leppik I E. *Contemporary Diagnosis and Management of the Patient With Epilepsy*. 4$^{th}$ Ed., Newtown, Pa.: Handbooks in Health Care Co (1999).

Generalized tonic-clonic seizures (also called "grand mal") are the ones most commonly identified with epilepsy and are the most dramatic. They can occur at any age but are rare in very young infants. See Morton et al., "Diagnosis and treatment of epilepsy in children and adolescents", *Drugs*. 51:399–414 (1996). They start with a sudden-onset tonic phase, typically lasting less than a minute, and all of the skeletal muscles contract at once, causing the patient to fall stiffly. In addition, the patient's diaphragm and chest muscles will contract, forcing out air in an sigh or "epileptic cry." During the clonic phase, the patient may clench the jaws, biting the inside of the cheek or side of the tongue with the molars, and consciousness may not return for 10 to 15 minutes. The patient will often be left feeling confusion, fatigue, and headache, which can last several hours to several days. See, Leppik I E. *Contemporary Diagnosis and Management of the Patient With Epilepsy.* 4th Ed., Newtown, Pa.: Handbooks in Health Care Co (1999).

Atonic seizures result in a sudden loss of postural tone, causing the patient to fall. In a few seconds, the patient will regain full consciousness. Atonic seizures are commonly associated with other seizure types and are common in Lennox-Gastaut syndrome. See, Leppik I E. *Contemporary Diagnosis and Management of the Patient With Epilepsy.* 4th Ed., Newtown, Pa.: Handbooks in Health Care Co (1999).

Other epileptic conditions include juvenile myoclonic epilepsy and Lennox-Gastaut syndrome. Juvenile myoclonic epilepsy often begins during the teenage years, and is a generalized, idiopathic epileptic syndrome, often exhibiting three seizure types: myoclonic, absence, and generalized tonic-clonic. Many patients will manifest clumsiness or jitters, which are exacerbated by stress. Lennox-Gastaut syndrome may be symptomatic (brain lesion identified) or cryptogenic (brain lesion assumed), and the generalized syndrome may include atypical absence, tonic, atonic, and tonic-clonic seizures. Often, patients suffering from Lennox-Gastaut syndrome will have varying degrees of psychomotor retardation. See, Leppik I E. *Contemporary Diagnosis and Management of the Patient With Epilepsy.* 4th Ed., Newtown, Pa.: Handbooks in Health Care Co (1999); and Beaumanoir et al., "The Lennox-Gastaut syndrome", In: Roger et al., "Epileptic Syndromes in Infancy, Childhood, and Adolescence", 2nd Ed., London, England: John Libby, pp. 231–244 (1992).

Currently, there are a number of drugs available that are used to treat epilepsy or epileptic conditions, and they are commonly referred to as anticonvulsants or antiepileptics. These drugs include older anticonvulsants, such as phenobarbital, primidone, and phenytoin, and more recent anticonvulsants, such as carbamazepine; valproic acid; felbamate; gabapentin; lamotrigine; tiagabine; topiramate; levetiracetam, and oxacarbazepine. In most cases, the newer anticonvulsants are approved as adjunctive therapy for use in conjunction with other anticonvulsants, although some of these have been approved or demonstrated efficacy as a monotherapy. See U.S. Pat. No. 6,309,406.

Common tremors, including essential, familial, and senile tremors, are relatively common in people over forty, but can also result from or be made worse by stimulants (e.g., caffeine) or during periods of stress or anxiety. In the beginning, tremors may be localized in the upper extremities, such as the hands, but can also include movements or nodding of the head, with both often occurring as a patient ages. In addition, the lips, tongue, jaw, and larynx may be involved in tremors, and they can sometimes result in a noticeable quiver in the voice of the patient.

The most common treatment for tremors are beta-blockers (e.g., propanolol) and sedatives (such as benzodiazepines and barbituates). In addition, some patients may "self-medicate" using alcohol due to its sedative properties.

2.3. Obesity

Obesity is one of the most prevalent medical disorders afflicting humans today, affecting more than 30% of the population. Obesity can result in a number of other medical conditions or complications, including hypertension, cardiovascular disease, diabetes mellitus, insulin resistance, sleep apnea, cholecystitis, osteoarthritis, and cancer. Body mass index, or BMI, is common used to measure obesity, and is calculated by dividing the patient's weight in kilograms divided by their height in meters squared. The severity or degree of obesity is then determined by comparing a patient's BMI with standard deviations above the BMI means for males and females.

At present, scientists do not know the exact etiology of obesity, although generally it occurs when energy intake exceeds energy expenditure. In addition, it appears that genetic predisposition may play a role in the amount and distribution of body fat in a patient, and this may also be under some hormonal control.

2.4. Neuropathic Pain

Neuropathic pain describes pain that is associated with damage or permanent alteration of the peripheral or central nervous system. Neuropathic pain includes, but is not limited to, neuralgia, trigeminal neurologia, diabetic neuropathy and other forms of nerve damage, allodynia, paraesthesia, hyperaesthesia, phantom pain, phantom limb pain, hyperalgesia, and tinnitus. See Taylor and Meldrum, *Trends Pharmacol. Sci.*, 16:309–316 (1995); and Simpson and Davies, *Trends Pharmacol. Sci.*, 20:12–18 (1999). Clinical manifestations of neuropathic pain include a sensation of burning or electric shock, feelings of bodily distortion, allodynia and hyperalgesia. The term allodynia describes the phenomenon of the perception of stimuli which are not painful per se, such as contact or heat/cold, as pain. See Rogers and Valley, *Clin Podiatr Med Surg.*, 11(1): 73–83 (January 1994). 2.5. Other Disorders Manic-depressive illnesses, such as manic-depressive bipolar disorder, are progressive psychiatric disorders of unknown etiology, although there are some hypotheses that recurrences of manic-depressive illness arise by electrophysiologic kindling. See, Goodwin and Jamison, *Manic-Depressive Illness*, Oxford University Press, New York, pp. 405–407 (1990). It is believed that topiramate may be useful in treating manic-depressive illnesses, as it has been shown to be effective in blocking kindled seizures in rats. See U.S. Pat. No. 5,753,693; and Wauquier et al., *Epilepsy Res.*, 24:73–77 (1996).

Migraine is a neurological disorder that is characterized by recurrent attacks of headache, with pain most often occurring on one side of the head, accompanied by various combinations of symptoms such as nausea, vomiting, and sensitivity to light and sound. The migraine can occur at any time of day or night, but occurs most frequently on arising in the morning. Routine activity or slight head movement typically makes the pain worse. These episodes can last from several hours to several days and are often disabling. During the attack the pain may migrate from one part of the head to another, and may radiate down the neck into the shoulder. Scalp tenderness occurs in the majority of patients during or after an attack.

Migraine with aura, or classic migraine, refers to a severe, throbbing headache that is often preceded by visual, motor, or sensory symptoms, called an "aura." Migraines can also occur without an aura, which is called common migraine.

Migraine is familial and often hereditary, and is most common in women, particularly young adult women. Common characteristics of migraine include: moderate to severe headache lasting from four to 72 hours; pain that is often, but not always, located on one side of the head and throbbing; pain is aggravated by moving or physical activity; pain is often accompanied with nausea, vomiting, sensitivity to light, sound, and odors. Following a migraine attack, many patients will feel tired, washed out, irritable, or listless or have impaired concentration.

There are a number of drugs that are currently available for prophylactic treatment of migraine, including propanolol, amitriptyline, valproate, phenelzine, and methysergid, as well as aspirin-like drugs, including aspirin, naproxen, ibuprofen, mefenamic acid, flufenamic acid, and tolfenamic acid. Typically, these drugs must be taken daily, and some are associated with severe adverse effects or the high dosage amounts required for effectiveness make them undesirable. In any event, the estimated probability of success with any one of these prophylactic antimigraine drugs is about 60 to 75%. See, *Harrison's Principles of Internal Medicine*, eds. Isselbacher et al., McGraw-Hill, Inc., New York, p. 69 (1994).

Cluster headache (also called "migrainous neuralgia") has been recognized for over 100 years, although the condition has been given many different names, such as erythroprosopalgia, Raeder's syndrome, spenopalatine neuralgia, ciliary neuralgia, vidian neuralgia, and histamine cephalalgia. There are several types of cluster headaches, including: the episodic type, which is the most common, is characterized by one to three short-lived attacks of periorbital pain per day over a 4 to 8 week period, followed by a pain-free interval; the chronic form, also called chronic migrainous neuralgia, which may begin without previous occurrence of episodic type cluster headache, or several years after an episodic pattern, and is characterized by the absence of sustained periods of remission. See A. Kudrow, "The pathogenesis of a cluster headache", *Curr. Opin. Neurol.*, 7:278–282 (1994).

The pain associated with a cluster headache starts quickly, without warning, and is often excruciating in intensity, and is deep, nonfluctuating, and explosive in quality; only occasionally is it pulsatile. Pain usually begins in, around, or above the eye or the temple, although occasionally the face, neck, ear, or hemicranium may be affected. It is always unilateral, and generally affects the same side in subsequent bouts. Periodicity is a characteristic feature in most cluster headache patients, with attacks lasting from ten minutes to several hours, often repeating in very close intervals, and many also experience additional attacks that occur randomly throughout the day.

The most common associated symptom of cluster headache is lacrimation from the eye on the affected side. In addition, a blocked nasal passage, rhinorrhea, red eye, and sweating and pallor of the forehead and cheek are often found, but their absence does not exclude the diagnosis. A transitory, partial Homer's syndrome (pupillary miosis and lid ptosis) occurs in two-thirds of patients when they are examined during attacks, and is highly characteristic of the cluster headache syndrome and, after repeated occurrences, may become a permanent feature.

Cluster headache more often afflicts men than women, and most patients begin experiencing headache between the ages of 20 and 50 years, though cluster headaches can start to occur as early as the first decade and as late as the eighth decade.

3. SUMMARY OF THE INVENTION

This invention encompasses salts of topiramate, and polymorphs, solvates, hydrates, dehydrates, co-crystals, anhydrous, and amorphous forms thereof. The invention further encompasses pharmaceutical compositions and dosage forms comprising pharmaceutically acceptable salts of topiramate, and polymorphs, solvates, hydrates, dehydrates, co-crystals, anhydrous, and amorphous forms thereof. Specific salts encompassed by the invention include, but are not limited to, topiramate sodium, topiramate lithium, and topiramate potassium. Specific co-crystals encompassed by the invention include, but are not limited to, co-crystals or complexes of caffeine. Certain pharmaceutical compositions and dosage forms of the invention also comprise at least one additional anticonvulsant or antiepileptic agent.

The invention further provides methods of treating and preventing conditions in a patient that include, but are not limited to, seizures, convulsions, epileptic conditions, tremors, cerebral function disorders, obesity, neuropathic pain, affective disorders, migraines, and cluster headaches. Methods of the invention comprise administering to a patient in need of such treatment or prevention a therapeutically or prophylactically effective amount of a pharmaceutically acceptable salt of topiramate, or a polymorph, solvate, hydrate, dehydrate, co-crystal, anhydrous, and amorphous form thereof. In a preferred embodiment, the topiramate salt is topiramate sodium, topiramate lithium, topiramate potassium, or a polymorph, solvate, hydrate, dehydrate, co-crystal, anhydrous, or amorphous form thereof. Specific co-crystals of topiramate salts are co-crystals or complexes of caffeine.

Additional methods of the invention comprise adjunctively administering to a patient a therapeutically or prophylactically effective amount of a pharmaceutically acceptable salt of topiramate, or a polymorph, solvate, hydrate, dehydrate, co-crystal, anhydrous, and amorphous form thereof, and at least one additional anticonvulsant or antiepileptic agent.

3.1. Definitions

As used herein and unless otherwise indicated, the term "patient" includes mammals, and preferably humans.

As used herein and unless otherwise indicated, the term "topiramate" refers to 2,3:4,5-Di-O-isopropylidene-β-D-fructopyranose sulfamate and isomers and mixtures of isomers thereof. In particular, while "topiramate" conventionally refers to the specific compound named 2,3:4,5-Di-O-isopropylidene-β-D-fructopyranose sulfamate and represented by formula I, above, the term is used herein to refer to all enantiomerically and/or diastereomerically pure isomers of that specific compound, as well as mixtures of such isomers. In other words, the term "topiramate," as used herein unless otherwise indicated, encompasses sulfamic acid 2,2,7,7-tetramethyl-tetrahydro-bis[1,3]dioxolo[4,5-b;4',5'-d]pyran-3a-ylmethyl ester, which is represented by formula II:

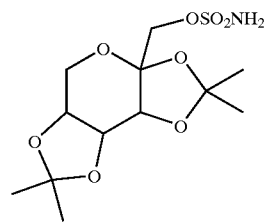

and enantiomerically and diastereomerically pure forms thereof, as well as mixtures of such forms. Specific mixtures comprise about 10, 20, 30, 40, or 50 weight percent one enantiomer or diastereomer and about 90, 80, 70, 60, or 50 weight percent of another enantiomer or diastereomer of the compound.

As used herein and unless otherwise indicated, the term "salt" encompasses salts that are pharmaceutically acceptable, as well as those that are not. Salts that are not pharmaceutically acceptable are preferably not administered to patients, but may be used to provide, for example, intermediate or bulk forms of drugs.

As used herein and unless otherwise indicated, the terms "pharmaceutically acceptable salt" or "pharmaceutically acceptable base addition salt" refers to a salt prepared with various pharmaceutically acceptable bases. Bases that can be used to prepare pharmaceutically acceptable salts are those that form non-toxic base addition salts, i.e., salts containing pharmacologically acceptable cations, such as, but not limited to, sodium, potassium, lithium, magnesium, calcium, aluminum, zinc, procaine, benzathine, chloroprocaine, choline, diethylamine, ethylenediamine, N-methylglucamine, benethamine, clemizole, dietheylamine, piperazine, tromethamine, triethylamine, ethanolamine, triethanolamine, arginine, lysine, histidine, tributylamine, 2-amino-2-pentylpropanol, 2-amino-2-methyl-1,3-propanediol, tris(hydroxymethyl) aminomethane, benzylamine, 2-(dimethylamino)ethanol, barium or bismuth counter ions. Particularly preferred cations are sodium, lithium, and potassium. The most preferred cation is sodium.

As used herein and unless otherwise indicated, the term "adjunctively administering" refers to the administration of one or more compounds or active ingredients in addition to a pharmaceutically acceptable salt of topiramate, or polymorph, solvate, hydrate, dehydrate, co-crystal, anhydrous, or amorphous form thereof, either simultaneously with the same or at intervals prior to, during, or following administration of the pharmaceutically acceptable salt of topiramate to achieve the desired therapeutic or prophylactic effect.

As used herein, the term "seizures" includes but is not limited to, partial seizures, including without limitation: simple partial seizures, complex partial seizures, and secondarily generalized seizures; generalized seizures, including without limitation absence seizures (also called "petit mal") typical absence seizures, atypical absence seizures, myoclonic seizures, tonic seizures, clonic seizures, generalized tonic-clonic seizures (also called "grand mal"), and atonic seizures; and seizures associated with juvenile myoclonic epilepsy and Lennox-Gastaut syndrome.

As used herein and unless otherwise indicated, the term "epileptic condition" refers to epilepsy, juvenile myoclonic epilepsy, and Lennox-Gastaut syndrome.

As used herein and unless otherwise indicated, the term "cerebral function disorder" includes, but is not limited to, disorders involving intellectual deficits such as senile dementia, Alzheimer's type dementia, memory loss, amnesia/amnesic syndrome, disturbances of consciousness, coma, lowering of attention, speech disorders, Parkinson's disease, autistic disorder, autism, hyperkinetic syndrome, and schizophrenia. Also within the meaning of the term are disorders caused by cerebrovascular diseases (including, but not limited to, cerebral infarction, cerebral bleeding, cerebral arteriosclerosis, cerebral venous thrombosis, head injuries, and the like) where symptoms include disturbance of consciousness, senile dementia, coma, lowering of attention, and speech disorders.

As used herein and unless otherwise indicated, the term "method of treating Parkinson's disease" means relief from the symptoms of Parkinson's disease, which include, but are not limited to, a slowly increasing disability in purposeful movement, tremors, bradykinesia, ticks, rigidity, and posture disturbance.

As used herein and unless otherwise indicated, the term "tremors" refers to familial, essential and senile tremors.

As used herein and unless otherwise indicated, the term "a method for treating obesity or weight gain" means reduction of weight, relief from being overweight, relief from gaining weight, or relief from obesity, all of which are usually due to extensive consumption of food.

As used herein and unless otherwise indicated, the term "neuropathic pain" includes, but is not limited to, neuralgia, trigeminal neurologia, diabetic neuropathy and other forms of nerve damage, allodynia, paraesthesia, hyperaesthesia, phantom pain, phantom limb pain, hyperalgesia, and tinnitus.

As used herein and unless otherwise indicated, the term "affective disorder" includes, but is not limited to, manic conditions (e.g., acute mania), manic rapid cycling, bipolar mood disorders or conditions (e.g., manic-depressive bipolar disorder), mood stabilization, post-traumatic stress disorder, depression, anxiety disorders, attention deficit disorder, attention deficit disorder with hyperactivity, compulsive or obsessive-compulsive disorder, narcolepsy, premenstrual syndrome, chronic fatigue syndrome, seasonal affective disorder, substance abuse or addiction, nicotine addiction or craving, and obesity or weight gain.

As used herein and unless otherwise indicated, the terms "attention deficit disorder" (ADD), "attention deficit disorder with hyperactivity" (ADDH), and "attention deficit/hyperactivity disorder" (AD/HD), are used in accordance with their accepted meanings in the art. See, e.g., *Diagnostic and Statistical Manual of Mental Disorders,* Fourth Ed., American Psychiatric Association, 1997 (DSM-IV™); and *Diagnostic and Statistical Manual of Mental Disorders,* $3^{rd}$ Ed., American Psychiatric Association (1981) (DSM-III™).

As used herein and unless otherwise indicated, the term "depression" includes a disease or condition characterized by changes in mood, feelings of intense sadness, despair, mental slowing, loss of concentration, pessimistic worry, agitation, and self-deprecation. Physical symptoms of depression that may be reduced or alleviated by the methods of the invention include, but are not limited to, insomnia, anorexia, weight loss, decreased energy and libido, and abnormal hormonal circadian rhythms.

As used herein and unless otherwise indicated, the term "cluster headache" includes, but is not limited to, migrainous neuralgia, chronic migrainous neuralgia, erythroprosopalgia, Raeder's syndrome, spenopalatine neuralgia, ciliary neuralgia, vidian neuralgia, histamine cephalalgia, episodic cluster headache, and chronic cluster headache.

3.2. Brief Description of the Drawings

Novel aspects of specific embodiments of the invention can be better understood with reference to the figures described below:

FIGS. 1–3 relate to analysis of topiramate sodium trihydrate synthesized in Example 1. Specifically, FIG. 1 shows the powder X-ray diffraction pattern of the compound, FIG. 2 shows the differential scanning calorimetric (DSC) analysis for the compound, and FIG. 3 shows the thermogravimetric analysis (TGA) of the compound.

FIG. 4 relates to analysis of topiramate sodium trihydrate synthesized in Example 2 using Raman spectroscopy, and the Raman spectrum for the compound is shown.

Figure 8:
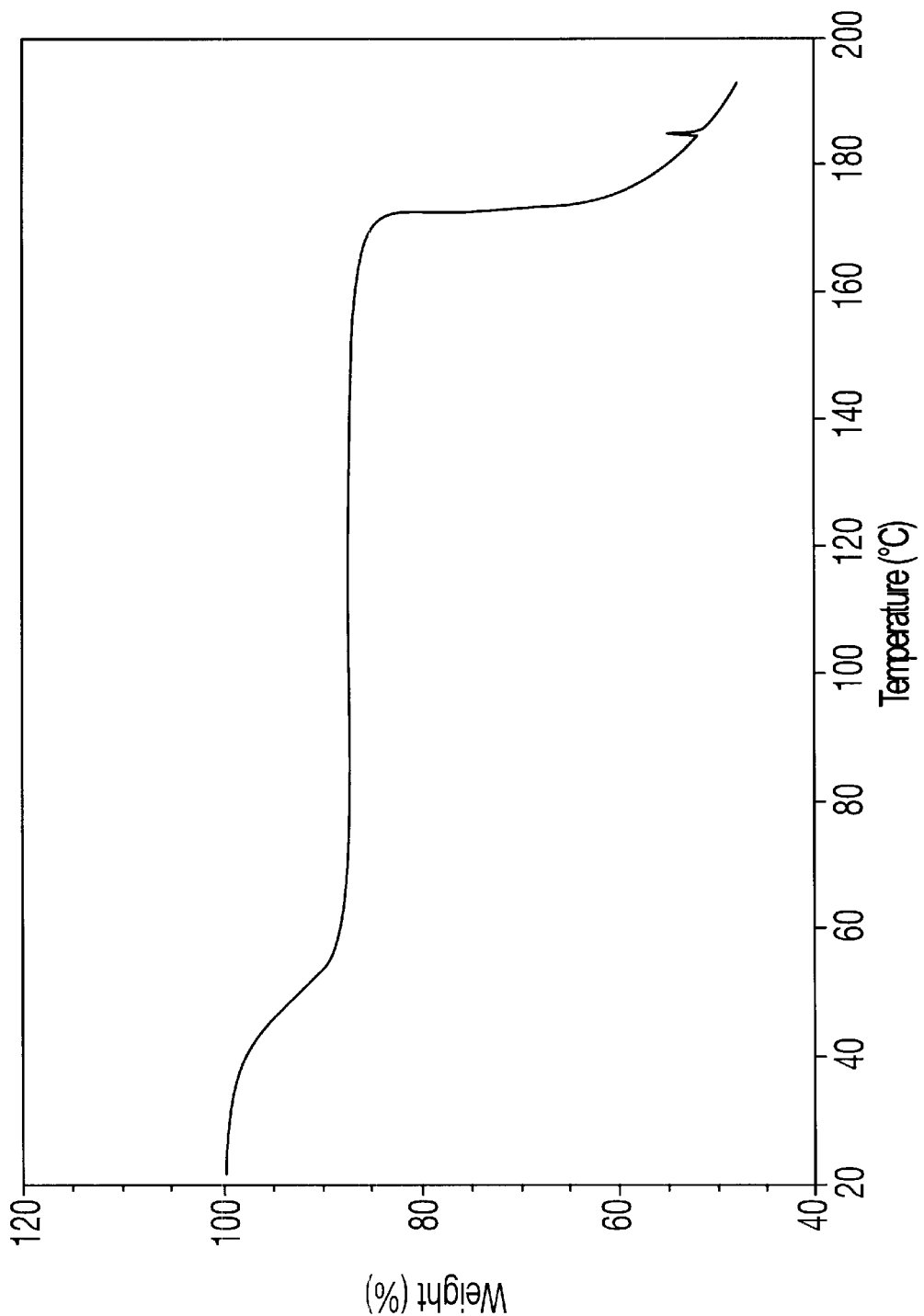
Figure 9:
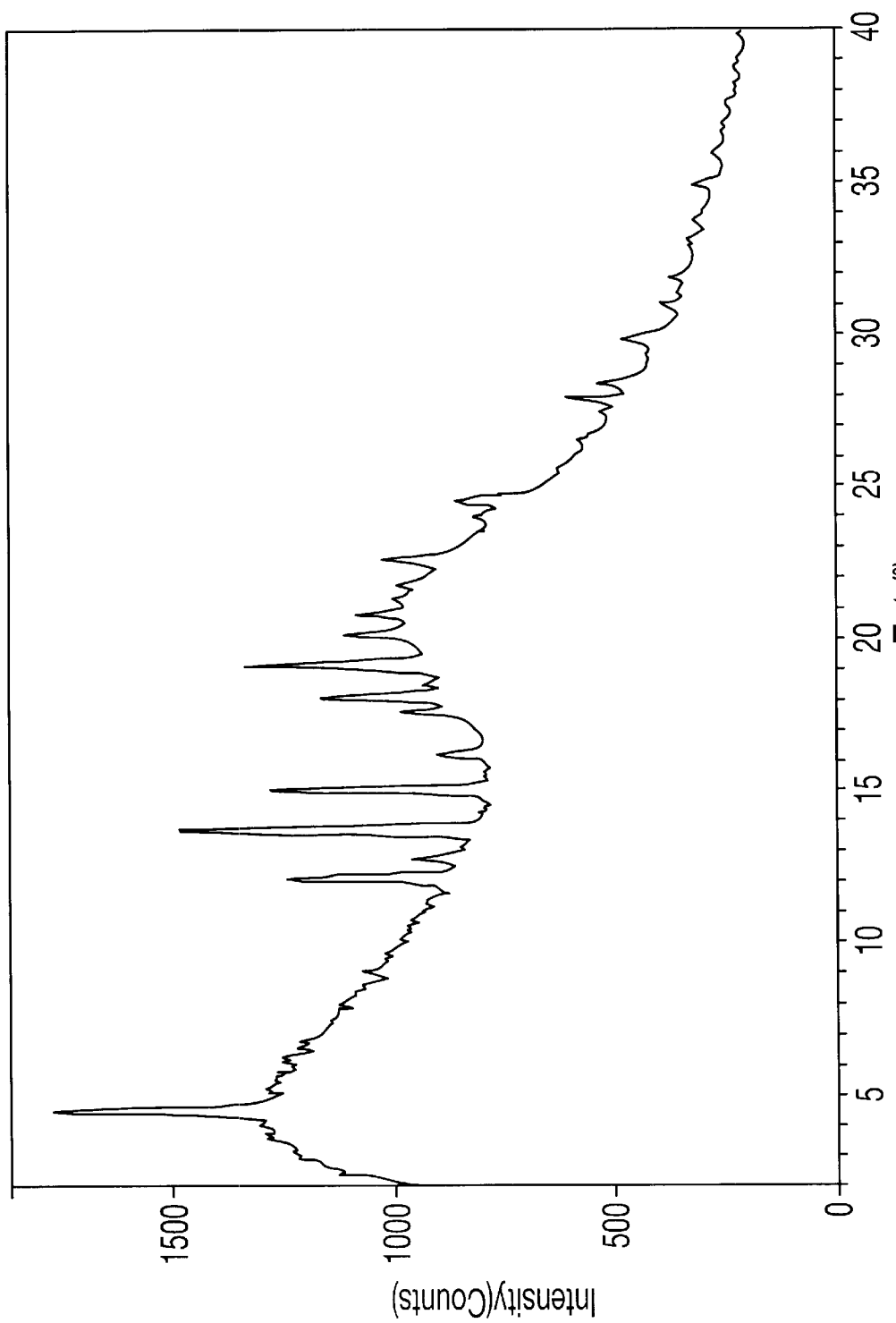

FIGS. 8 and 9 relate to analysis of topiramate sodium trihydrate synthesized in Example 3. Specifically, FIG. 8 shows the thermogravimetric analysis (TGA) of the compound, and FIG. 9 shows an powder X-ray diffraction pattern of the compound.

Figure 10:
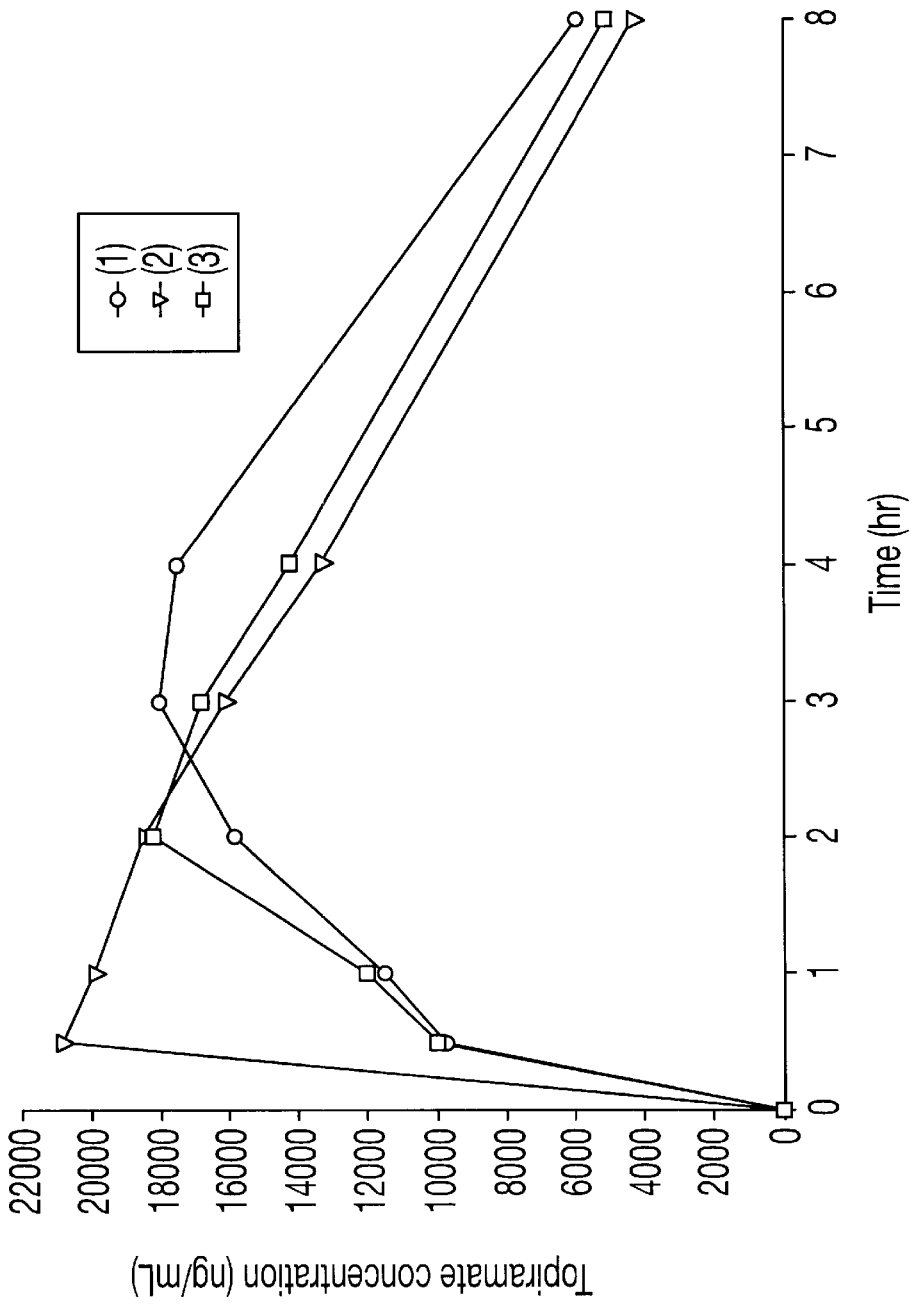

FIG. 10 shows the pharmacokinetics in rats after 30 mg/kg oral doses of topiramate crystal form as compared to topiramate sodium trihydrate and topiramate sodium trihydrate with added tartaric acid.

Figure 11:
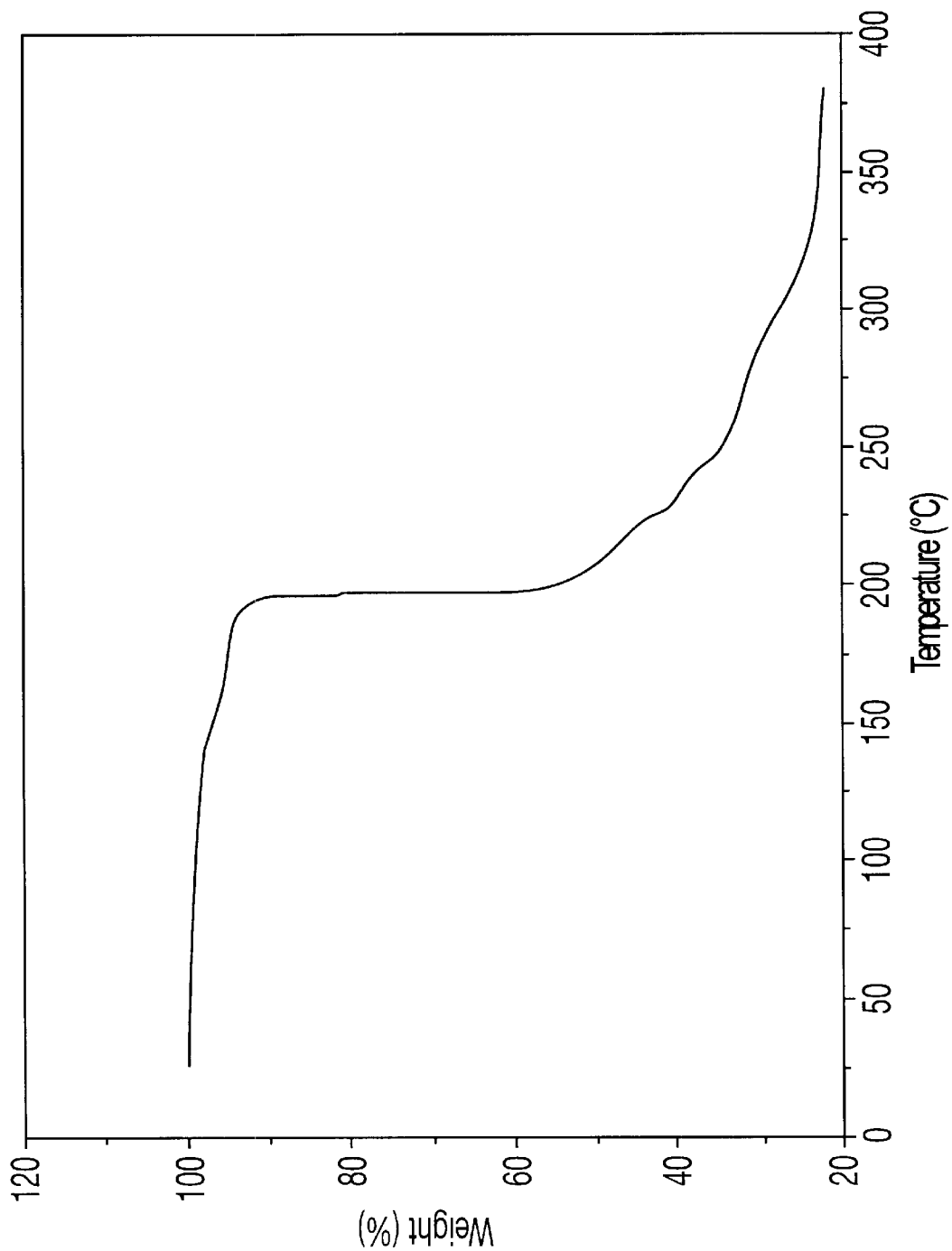
Figure 12:
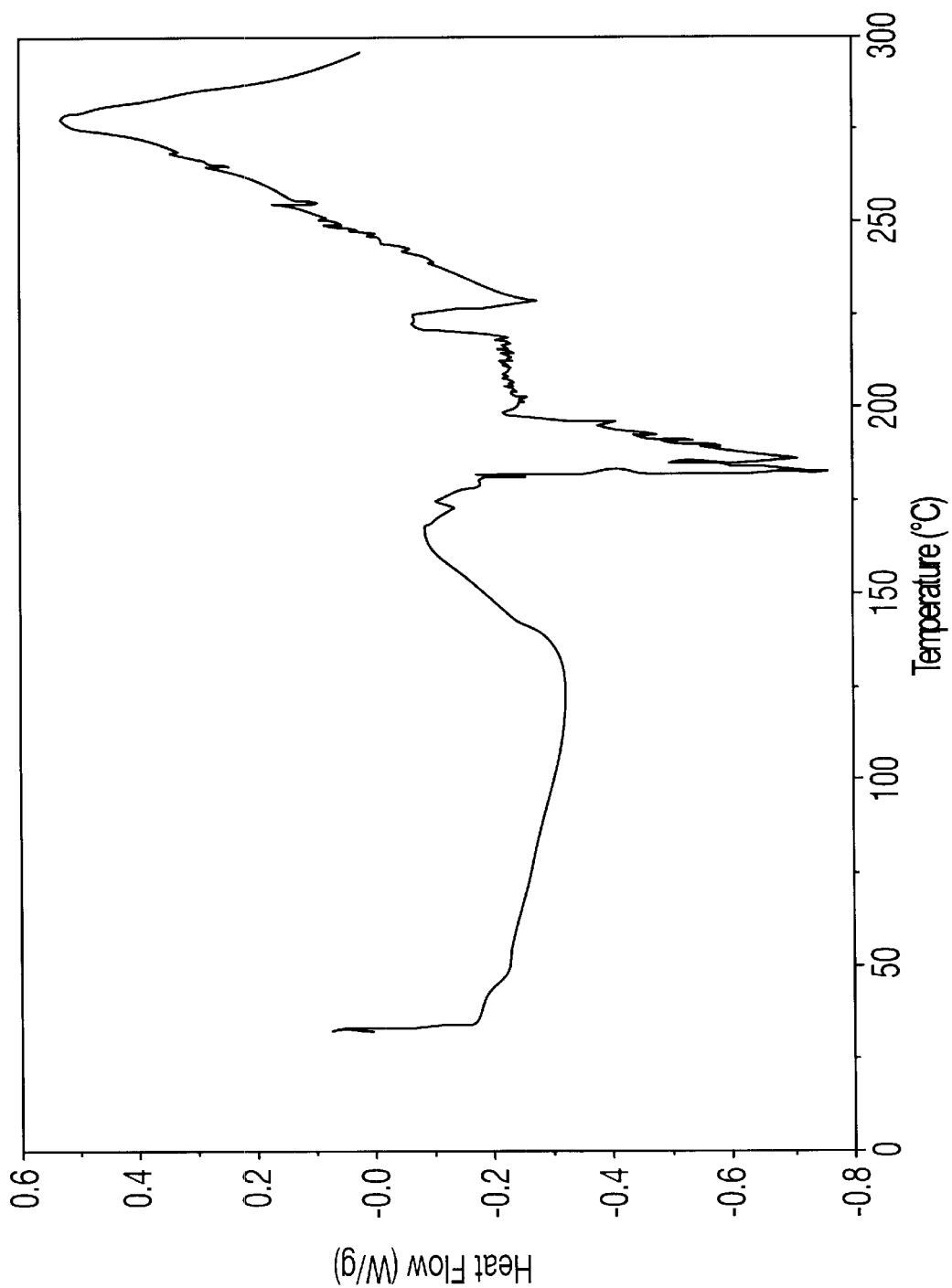

FIGS. 11 and 12 relate to analysis of topiramate lithium. Specifically, FIG. 11 shows the thermogravimetric analysis (TGA) of the compound, and FIG. 12 shows the differential scanning calorimetric (DSC) analysis for the compound.

Figure 13:
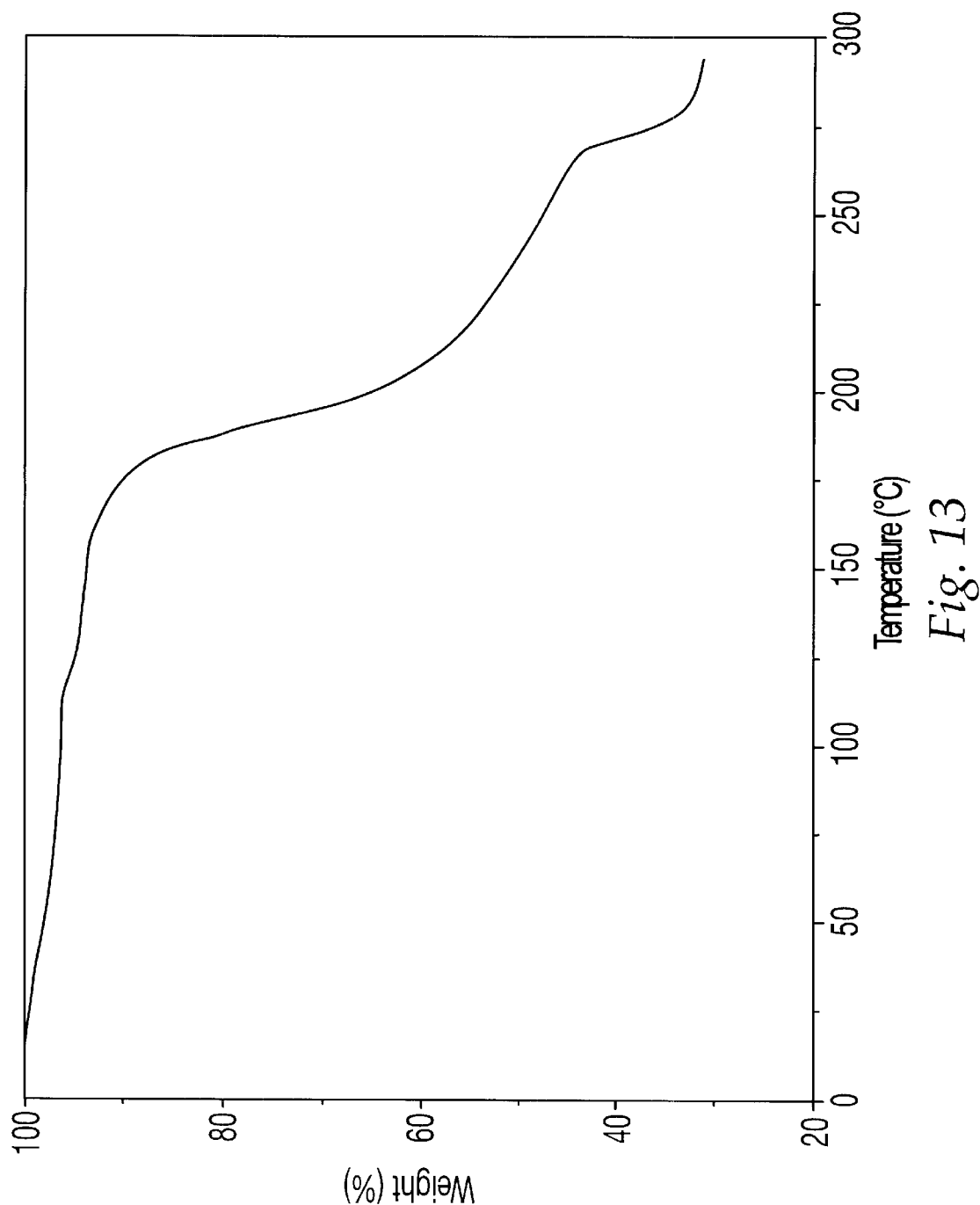

FIG. 13 shows the thermogravimetric analysis (TGA) of topiramate potassium.

4. DETAILED DESCRIPTION OF THE INVENTION

This invention relates to salts of topiramate and polymorphs, solvates (e.g., hydrates and mixed solvates, as well as hydrates of salts), dehydrates, co-crystals (e.g., with other compounds, as well as with other salts or forms of topiramate), anhydrous and amorphous forms thereof, pharmaceutical compositions and dosage forms comprising pharmaceutically acceptable salts of topiramate and polymorphs, solvates, hydrates, dehydrates, co-crystals, anhydrous and amorphous forms thereof, and their use to treat or prevent a variety of diseases, conditions, or disorders in a patient, and humans in particular.

One embodiment of the invention encompasses a base-addition salt of topiramate, or a polymorph, solvate, hydrate, dehydrate, co-crystal, anhydrous, or amorphous forms thereof. Preferably, the base-addition salt of topiramate is a pharmaceutically acceptable salt, and more preferably, the base-addition salt is topiramate sodium, topiramate lithium, or topiramate potassium, or a polymorph, solvate, hydrate, dehydrate, co-crystal, anhydrous, or amorphous form thereof.

Another embodiment of the invention encompasses a form of topiramate that has an aqueous solubility at 25° C. of greater than about 10, 20, 50, 100, 250, 500, 750, 1000, 1100, or 1250 mg/ml. In a specific embodiment, that form is a topiramate salt, or a polymorph, solvate, hydrate, dehydrate, co-crystal, anhydrous, or amorphous form thereof. A specific salt is topiramate sodium. Preferably, the topiramate sodium is topiramate sodium trihydrate.

Another embodiment of the invention encompasses pharmaceutically acceptable salts of topiramate, or a polymorph, solvate, hydrate, dehydrate, co-crystal, anhydrous, or amorphous form thereof. In a preferred embodiment, the pharmaceutically acceptable salt of topiramate is topiramate sodium, topiramate lithium, topiramate potassium, or a polymorph, solvate, hydrate, dehydrate, co-crystal, anhydrous, or amorphous form thereof. More preferably, the pharmaceutically acceptable salt of topiramate is topiramate sodium, or a polymorph, solvate, hydrate, dehydrate, co-crystal, anhydrous, or amorphous form thereof. Preferably, the topiramate sodium is topiramate sodium trihydrate.

Another embodiment of the invention encompasses pharmaceutical compositions and dosage forms comprising a therapeutically or prophylactically effective amount of a pharmaceutically acceptable salt of topiramate, or a polymorph, solvate, hydrate, dehydrate, co-crystal, anhydrous, or amorphous form thereof. Preferably, the pharmaceutically acceptable salt of topiramate is topiramate sodium, topiramate lithium, topiramate potassium, or a polymorph, solvate, hydrate, dehydrate, co-crystal, anhydrous, or amorphous form thereof, and more preferably, the pharmaceutically acceptable salt of topiramate is topiramate sodium, or a polymorph, solvate, hydrate, dehydrate, co-crystal, anhydrous, or amorphous form thereof. In another embodiment, the pharmaceutical compositions and dosage forms can contain one or more pharmaceutically acceptable excipients or a carrier.

In one preferred embodiment, the pharmaceutically acceptable salt of topiramate is topiramate sodium, and the dosage form is a tablet. Preferably, the topiramate sodium is a hydrate such as, but not limited to, topiramate sodium trihydrate, or a polymorph thereof.

In another preferred embodiment, the pharmaceutically acceptable salt of topiramate is in a dosage form that is a controlled-release or extended release dosage form. In one aspect, the controlled-release dosage form of the invention is an oral osmotic pump form (e.g., tablet or capsule). Preferably, the pharmaceutically acceptable salt of topiramate in said dosage forms is topiramate sodium, topiramate lithium, or topiramate potassium.

This invention also encompasses a controlled release pharmaceutical dosage form comprising topiramate, or a pharmaceutically acceptable salt, polymorph, solvate, hydrate, dehydrate, co-crystal, anhydrous, or amorphous form thereof, and a pharmaceutically acceptable excipient. Preferably, the controlled release dosage form is an oral osmotic pump form (e.g., tablet or capsule). Preferably, the topiramate, or polymorph, solvate, hydrate, dehydrate, co-crystal, anhydrous, or amorphous form thereof, has an aqueous solubility at 25° C. of greater than about 10, 20, 50, 100, 250, 500, 750, 1000, 1100, or 1250 mg/ml.

A further embodiment of the invention encompasses a method of treating or preventing seizures or convulsions in a patient which comprises administering to a patient in need of such treatment or prevention a therapeutically or prophylactically effective amount of a pharmaceutically acceptable salt of topiramate, or a polymorph, solvate, hydrate, dehydrate, co-crystal, anhydrous, or amorphous form thereof. Preferably, the pharmaceutically acceptable salt of topiramate is topiramate sodium, topiramate lithium, topiramate potassium, or a polymorph, solvate, hydrate, dehydrate, co-crystal, anhydrous, or amorphous form thereof, and more preferably, the pharmaceutically acceptable salt of topiramate is topiramate sodium, or a polymorph, solvate, hydrate, dehydrate, co-crystal, anhydrous, or amorphous form thereof.

In one preferred embodiment, the pharmaceutically acceptable salt of topiramate is topiramate sodium. Preferably, the topiramate sodium is a hydrate such as, but not limited to, topiramate sodium trihydrate, or a polymorph thereof.

Another embodiment of the invention encompasses a method of treating or preventing an epileptic condition in a patient which comprises administering to a patient in need of such treatment or prevention a therapeutically or prophylactically effective amount of a pharmaceutically acceptable salt of topiramate, or a polymorph, solvate, hydrate, dehydrate, co-crystal, anhydrous, or amorphous form thereof. Preferably, the pharmaceutically acceptable salt of topiramate is topiramate sodium, topiramate lithium, topiramate potassium, or a polymorph, solvate, hydrate, dehydrate, co-crystal, anhydrous, or amorphous form thereof, and more preferably, the pharmaceutically acceptable salt of topiramate is topiramate sodium, or a polymorph, solvate, hydrate, dehydrate, co-crystal, anhydrous, or amorphous form thereof.

In one preferred embodiment, the pharmaceutically acceptable salt of topiramate is topiramate sodium. Preferably, the topiramate sodium is a hydrate such as, but not limited to, topiramate sodium trihydrate, or a polymorph thereof.

In another method encompassed by these embodiments, the pharmaceutically acceptable salt of topiramate is adjunctively administered with another anticonvulsant or antiepileptic, i.e., the pharmaceutically acceptable salt of topiramate and additional anticonvulsant or antiepileptic are administered as a combination, concurrently but separately, or sequentially by any suitable route (e.g., orally, parenterally, transdermally, or mucosally). Additional anticonvulsants or antiepileptics include, but are not limited to, carbamazepine, phenytoin, ethotiagabine, valproic acid, ethosuximide, felbamate, gabapentin, lamotrigine, levetiracetam, and oxcarbazepine.

Another embodiment of the invention encompasses a method for treating or preventing tremors in a patient which comprises administering to a patient in need of such treatment or prevention a therapeutically or prophylactically effective amount of a pharmaceutically acceptable salt of topiramate, or a pharmaceutically acceptable polymorph, solvate, hydrate, dehydrate, co-crystal, anhydrous, or amorphous form thereof.

In one preferred embodiment, the pharmaceutically acceptable salt of topiramate is topiramate sodium. Preferably, the topiramate sodium is a hydrate such as, but not limited to, topiramate sodium trihydrate, or a polymorph thereof.

Yet another embodiment of the invention encompasses a method of treating or preventing a cerebral function disorder which comprises administering to a patient in need of such treatment or prevention a therapeutically or prophylactically effective amount of a pharmaceutically acceptable salt of to, or a pharmaceutically acceptable polymorph, solvate, hydrate, dehydrate, co-crystal, anhydrous, or amorphous form thereof.

In one preferred embodiment, the pharmaceutically acceptable salt of topiramate is topiramate sodium. Preferably, the topiramate sodium is a hydrate such as, but not limited to, topiramate sodium trihydrate, or a polymorph thereof.

A further embodiment of the invention encompasses a method for treating or preventing obesity or weight gain in a patient which comprises administering to a patient in need thereof a therapeutically effective amount of a pharmaceutically acceptable salt of topiramate, or a polymorph, solvate, hydrate, dehydrate, co-crystal, anhydrous, or amorphous form thereof. Preferably, the pharmaceutically acceptable salt of topiramate is topiramate sodium, topiramate lithium, topiramate potassium, or a polymorph, solvate, hydrate, dehydrate, co-crystal, anhydrous, or amorphous form thereof, and more preferably, topiramate sodium, or a polymorph, solvate, hydrate, dehydrate, co-crystal, anhydrous, or amorphous form thereof.

In one preferred embodiment, the pharmaceutically acceptable salt of topiramate is topiramate sodium. Preferably, the topiramate sodium is a hydrate such as, but not limited to, topiramate sodium trihydrate, or a polymorph thereof.

Another embodiment of the invention encompasses a method for treating or preventing neuropathic pain in a patient which comprises administering to a patient in need of such treatment or prevention a therapeutically or prophylactically effective amount of a pharmaceutically acceptable salt of topiramate, or a pharmaceutically acceptable polymorph, solvate, hydrate, dehydrate, co-crystal, anhydrous, or amorphous form thereof. Preferably, the pharmaceutically acceptable salt of topiramate is topiramate sodium, topiramate lithium, topiramate potassium, or a polymorph, solvate, hydrate, dehydrate, co-crystal, anhydrous, or amorphous form thereof, and more preferably, topiramate sodium, or a polymorph, solvate, hydrate, dehydrate, co-crystal, anhydrous, or amorphous form thereof.

In one preferred embodiment, the pharmaceutically acceptable salt of topiramate is topiramate sodium. Preferably, the topiramate sodium is a hydrate such as, but not limited to, topiramate sodium trihydrate, or a polymorph thereof.

A further embodiment of the invention encompasses a method of treating or preventing an affective disorder in a patient which comprises administering to a patient in need of such treatment or prevention a therapeutically or prophylactically effective amount of a pharmaceutically acceptable salt of topiramate, or a polymorph, solvate, hydrate, dehydrate, co-crystal, anhydrous, or amorphous form thereof. Preferably, the pharmaceutically acceptable salt of topiramate is topiramate sodium, topiramate lithium, and topiramate potassium, or a polymorph, solvate, hydrate, dehydrate, co-crystal, anhydrous, or amorphous form thereof. Another aspect of this embodiment of the invention comprising a method of treating or prevention an affective disorder comprises administering to a patient in need of such treatment or prevention a therapeutically or prophylactically effective amount of a topiramate lithium, or a polymorph, solvate, hydrate, dehydrate, co-crystal, anhydrous, or amorphous form thereof.

In one preferred embodiment, the pharmaceutically acceptable salt of topiramate is topiramate sodium. Preferably, the topiramate sodium is a hydrate such as, but not limited to, topiramate sodium trihydrate, or a polymorph thereof.

Another embodiment of the invention comprises a method of eliciting smoking cessation in a patient which comprises administering to a patient in need thereof a therapeutically effective amount of a pharmaceutically acceptable salt of topiramate, or a polymorph, solvate, hydrate, dehydrate, co-crystal, anhydrous, or amorphous form thereof.

In one preferred embodiment, the pharmaceutically acceptable salt of topiramate is topiramate sodium. Preferably, the topiramate sodium is a hydrate such as, but not limited to, topiramate sodium trihydrate, or a polymorph thereof.

Yet another embodiment of the invention encompasses a method of treating migraine in a human patient which comprises administering to a patient in need of such treatment a therapeutically effective amount of a pharmaceutically acceptable salt of topiramate, or a pharmaceutically acceptable polymorph, solvate, hydrate, dehydrate, co-crystal, anhydrous, or amorphous form thereof. Another aspect of this embodiment comprises a method of reducing the frequency or severity of migraine in a human patient which comprises administering to the patient in need thereof an effective amount of a pharmaceutically acceptable salt of topiramate, or a pharmaceutically acceptable polymorph, solvate, hydrate, dehydrate, co-crystal, anhydrous, or amorphous form thereof. Preferably, the pharmaceutically acceptable salt of topiramate is topiramate sodium, topiramate lithium, topiramate potassium, or a polymorph, solvate, hydrate, dehydrate, co-crystal, anhydrous, or amorphous form thereof, and more preferably, the pharmaceutically acceptable salt of topiramate is topiramate sodium, or a polymorph, solvate, hydrate, dehydrate, co-crystal, anhydrous, or amorphous form thereof.

In one preferred embodiment, the pharmaceutically acceptable salt of topiramate is topiramate sodium. Preferably, the topiramate sodium is a hydrate such as, but not limited to, topiramate sodium trihydrate, or a polymorph thereof.

A further embodiment of the invention encompasses a method for treating or preventing cluster headache in a patient which comprises administering to a patient in need of such treatment or prevention a therapeutically or prophylactically effective amount of a pharmaceutically acceptable salt of topiramate, or a polymorph, solvate, hydrate, dehydrate, co-crystal, anhydrous, or amorphous form thereof. Preferably, the pharmaceutically acceptable salt of topiramate is topiramate sodium, topiramate lithium, topiramate potassium, or a polymorph, solvate, hydrate, dehydrate, co-crystal, anhydrous, or amorphous form thereof.

In one preferred embodiment, the pharmaceutically acceptable salt of topiramate is topiramate sodium. Preferably, the topiramate sodium is a hydrate such as, but not limited to, topiramate sodium trihydrate, or a polymorph thereof.

Another method encompassed by the invention comprises adjunctively administering the pharmaceutically acceptable salt of topiramate, or a polymorph, solvate, hydrate, dehydrate, co-crystal, anhydrous, or amorphous form thereof, with caffeine, wherein the pharmaceutically acceptable salt of topiramate and caffeine are administered as a combination, concurrently but separately, or sequentially by any suitable route (e.g., orally, parenterally, transdermally, or mucosally). In one aspect, caffeine and a pharmaceutically acceptable salt of topiramate, or a polymorph, solvate, hydrate, dehydrate, co-crystal, anhydrous, or amorphous form thereof, are administered in combination. Preferably, the pharmaceutically acceptable salt of topiramate is topiramate sodium, topiramate lithium, or topiramate potassium, or a polymorph, solvate, hydrate, dehydrate, co-crystal, anhydrous, or amorphous form thereof. More preferably, the pharmaceutically acceptable salt of topiramate is topiramate sodium, or a polymorph, solvate, hydrate, dehydrate, co-crystal, anhydrous, or amorphous form thereof.

In one preferred embodiment, the pharmaceutically acceptable salt of topiramate is topiramate sodium. Preferably, the topiramate sodium is a hydrate such as, but not limited to, topiramate sodium trihydrate, or a polymorph thereof.

Further embodiments of the invention comprise co-crystals or complexes of topiramate, pharmaceutical compositions and dosage forms comprising a therapeutically or prophylactically effective amount of a co-crystal or complex of topiramate, and methods of treating and preventing conditions in a patient, including without limitation migraine, cluster headache, neuropathic pain, affective disorders, obesity, seizures, convulsions, epileptic conditions, tremors, and cerebral function disorders. These methods comprise administering to a patient in need of such treatment or prevention a therapeutically or prophylactically effective amount of a co-crystal or complex of topiramate. Specific co-crystals or complexes include, but are not limited to, caffeine.

Topiramate can be made using various methods known to those skilled in the art. For example, methods for the chemical synthesis of topiramate are described in U.S. Pat. No. 4,513,006, which is incorporated by reference herein in its entirety. Other methods well known in the art for preparing topiramate may also be used, including, for example, those disclosed in U.S. Pat. Nos. 6,319,903, 5,387,700; 5,258,402, 5,384,327, 5,242,942, 4,792,569, 2,554,816 and 2,980,679, all of which are incorporated herein by reference in their entireties.

The present invention involves the unexpected discovery that the sulfamate ($-OSO_2NH_2$) group of topiramate is slightly acidic and thus may be a handle for generation of salts, co-crystals, and complexes with basic compounds such as, but not limited to, caffeine, N-methyl pyrrolidine, nicotine, nicotinamide, and ethers such as PEGs (examples include but are not limited to PEG 200 and PEG 300). Salts are often associated with improved chemical stability and increased solubility of drugs leading to better delivery of drug to the body, by reducing unwanted degradation product exposure and increasing levels of drug in the body. Salt forms of drugs therefore constitute a useful set of options for development of drug formulations.

Pharmaceutically acceptable salts of topiramate can be prepared by treating topiramate with appropriate bases, such as organic or inorganic bases. Bases that can be used to prepare pharmaceutically acceptable salts of topiramate are those that form non-toxic base addition salts, i.e., salts containing pharmacologically acceptable cations, including, but not limited to, sodium, potassium, lithium, magnesium, calcium, aluminum, zinc, procaine, benzathine, chloroprocaine, choline, diethylamine, ethylenediamine, N-methylglucamine, benethamine, clemizole, diethylamine, piperazine, tromethamine, triethylamine, ethanolamine, triethanolamine, arginine, lysine, histidine, tributylamine, 2-amino-2-pentylpropanol, 2-amino-2-methyl-1,3-propanediol, tris(hydroxymethyl)aminomethane, benzylamine, 2-(dimethylamino)ethanol, barium or bismuth counter ions. Particularly preferred cations are sodium, lithium, and potassium. The most preferred cation is sodium.

Crystallization of pharmaceutically acceptable salts of topiramate can be accomplished by several means, as would be apparent to one skilled in the art. For instance, saturation of an aqueous solution of the salt can be increased by cooling, and the cooling curve can be a determinant of the particle properties (e.g., size, habit) that result from a crystallization process. Alternatively, addition of an anti-solvent (or non-solvent), such as an alcohol or other water miscible solvent, can be used to increase saturation of the salt form in the medium and hence effect nucleation and growth of crystals. Examples of anti-solvents include, but are not limited to, iso-propanol, THF, and ethanol. Preferably, ethanol would be used, due to its azeotrope with water, anti-solvent quality with many salt forms, and pharmaceutical acceptance.

Co-crystals and complexes of topiramate and other compounds can be prepared using conventional crystallization techniques, e.g., from solutions comprising topiramate and the other compounds. Without being limited by theory, it is believed that the compounds within co-crystals and complexes can interact via hydrogen bonding, ionic, or other interactions. Crystallization from melts of topiramate and other compounds may also be used to prepare co-crystals or complexes of topiramate. For example, a co-crystal or complex of topiramate and caffeine can be prepared by melting and recrystallizing caffeine, allowing such to cool, then contacting topiramate melt with the recrystallized caffeine, and allowing this to cool. In a particular method, caffeine is melted and recrystallized between a glass slide and glass cover slip on a hot-stage microscope (such as a Mettler-Toledo FP950tstage mounted on a Zeiss Axioplan II polarized light microscope). The hot-stage is allowed to cool to about 30° C. Topiramate is then placed on a glass slide in contact with the edge of the glass cover slip. The solid topiramate is melted and the melt is allowed to come into contact with the recrystallized caffeine. The temperature of the hotstage is lowered (e.g., to about 70° C.) and held there overnight. During that time the melted topiramate recrystallizes and a cocrystalline phase crystallizes between the caffeine and topiramate regions. The slide can then be heated to determined the melting point of the caffeine:topiramate co-crystal.

The pharmaceutically acceptable salts of topiramate, or polymorphs, solvates, hydrates, dehydrates, co-crystals, anhydrous, and amorphous forms thereof, and pharmaceutical compositions and dosage forms thereof, of the invention possess potent activity as antiepileptics, anticonvulsants, anti-obesity agents, and mood stabilizers. For example, the pharmaceutically acceptable salts of topiramate, or polymorphs, solvates, hydrates, dehydrates, co-crystals, anhydrous, or amorphous forms thereof, and pharmaceutical compositions and dosage forms thereof, of the invention can be used to treat or prevent a variety of diseases and conditions including, but not limited to, seizures, epileptic conditions, tremors, obesity, cerebral function disorders, neuropathic pain, affective disorders, migraine, and cluster headaches.

4.1. Methods of Treatment and Prevention

The magnitude of a prophylactic or therapeutic dose of each active ingredient in the acute or chronic management of a disease or disorder will vary with the disease or disorder itself, the specific active ingredients, and the route of administration. The dose, dose frequency, or both, may also vary according to age, body weight, the severity of the condition or disease, response, and the past medical history of the patient. Suitable dosing regimens can be readily selected by the skilled artisan with due consideration of such factors by following, for example, dosages and dose regimens reported in the literature and recommended in the *Physician's Desk Reference®* ($56^{th}$ ed., 2002). Unless otherwise indicated, the magnitude of a prophylactic or therapeutic dose of the pharmaceutically acceptable salt of topiramate used in an embodiment of the invention will be that which is safe and effective (e.g., has received regulatory approval).

In one embodiment of the invention, the pharmaceutically acceptable salt of topiramate (e.g., topiramate sodium, topiramate lithium, or topiramate potassium) is administered as needed in an amount of from about 10 mg to about 1500 mg, preferably in an amount of from about 25 mg to about 1000 mg, more preferably in an amount from about 50 mg to about 75 mg, and most preferably in an amount of from about 100 mg to about 500 mg. When considering dosing and comparisons of clinical data resulting from the use of the pharmaceutically acceptable salts of topiramate of the invention, the skilled artisan will readily understand that the equivalents of topiramate in the salt form should be considered. For example, the ratio of molecular mass of topiramate sodium trihydrate to free form topiramate is 1.224, and thus a dose of about 122 mg of topiramate sodium trihydrate is equivalent to about 100 mg dose of topiramate. The dosage amounts and frequencies provided above are encompassed by the terms "therapeutically effective," "prophylactically effective," and "therapeutically or prophylactically effective" as used herein.

The suitability of a particular route of administration employed for a particular active ingredient will depend on the active ingredient itself (e.g., whether it can be administered orally without decomposing prior to entering the blood stream) and the disease or disorder to be treated or prevented. For example, topical administration is typically preferred for treating or preventing local diseases or disorders of the skin, while oral or parenteral administration is typically preferred for systemic diseases or disorders, or diseases or disorders within the body of the patient. Similarly, oral or parenteral administration may be preferred for the treatment or prevention of acute diseases or disorders, whereas transdermal or subcutaneous routes of administration may typically be employed for treatment or prevention of a chronic disease or disorder.

4.2. Pharmaceutical Compositions and Dosage Forms

Pharmaceutical compositions and dosage forms of the invention comprise a pharmaceutically acceptable salt of topiramate, or a pharmaceutically acceptable polymorph, solvate, hydrate, dehydrate, co-crystal, anhydrous, or amorphous form thereof. Specific salts of topiramate include, but are not limited to, topiramate sodium, topiramate lithium, and topiramate potassium, and hydrates thereof. Specific co-crystals of topiramate include, but are not limited to, co-crystals of caffeine, and hydrates thereof. Pharmaceutical compositions and unit dosage forms of the invention typically also comprise one or more pharmaceutically acceptable excipients or diluents. Advantages provided by specific compounds of the invention, such as, but not limited to, increased solubility and/or enhanced flow, purity, or stability (e.g., hygroscopicity) characteristics can make them better suited for pharmaceutical formulation and/or administration to patients than the prior art form of topiramate.

Pharmaceutical unit dosage forms of this invention are suitable for oral, mucosal (e.g., nasal, sublingual, vaginal, buccal, or rectal), parenteral (e.g., intramuscular, subcutaneous, intravenous, intraarterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease or disorder may contain larger amounts of the active ingredient than a dosage form used in the chronic treatment of the same disease or disorder. Similarly, a parenteral dosage form may contain smaller amounts of the active ingredient than an oral dosage form used to treat the same disease or disorder. These and other ways in which specific dosage forms encompassed by this invention will vary from one another will be readily apparent to those skilled in the art. See, e.g., *Remington's Pharmaceutical Sciences*, 18*th* ed., Mack Publishing, Easton, Pa. (1990).

Typical pharmaceutical compositions and dosage forms comprise one or more excipients. Suitable excipients are well known to those skilled in the art of pharmacy or pharmaceutics, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that comprise primary or secondary amines are particularly susceptible to such accelerated decomposition.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the invention may contain one or more solubility modulators, such as sodium chloride, sodium sulfate, sodium or potassium phosphate or organic acids. A specific solubility modulator is tartaric acid.

Like the amounts and types of excipients, the amounts and specific type of active ingredient in a dosage form may differ depending on factors such as, but not limited to, the route by which it is to be administered to patients. However, typical dosage forms of the invention comprise a pharmaceutically acceptable salt of topiramate, or a pharmaceutically acceptable polymorph, solvate, hydrate, dehydrate, co-crystal, anhydrous, or amorphous form thereof, in an amount of from about 10 mg to about 1000 mg, preferably in an amount of from about 25 mg to about 750 mg, and more preferably in an amount of from 50 mg to 500 mg.

4.2.1. Oral Dosage Forms

Pharmaceutical compositions of the invention that are suitable for oral administration can be presented as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of topiramate, and may be prepared by methods of pharmacy well known to those skilled in the art. See generally, *Remington's Pharmaceutical Sciences*, 18*th* ed., Mack Publishing, Easton, Pa. (1990).

Typical oral dosage forms of the invention are prepared by combining the pharmaceutically acceptable salt of topiramate in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents.

Due to their ease of administration, tablets and capsules represent the most advantageous solid oral dosage unit forms, in which case solid pharmaceutical excipients are used. If desired, tablets can be coated by standard aqueous or nonaqueous techniques. These dosage forms can be prepared by any of the methods of pharmacy. In general, pharmaceutical compositions and dosage forms are prepared by uniformly and intimately admixing the active ingredient (s) with liquid carriers, finely divided solid carriers, or both, and then shaping the product into the desired presentation if necessary.

For example, a tablet can be prepared by compression or molding. Compressed tablets can be prepared by compressing in a suitable machine the active ingredient(s) in a free-flowing form, such as a powder or granules, optionally mixed with one or more excipients. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, and AVICEL-PH-105 (available from FMC Corporation, American Viscose Division, Avicel Sales, Marcus Hook, Pa., U.S.A.), and mixtures thereof. An exemplary suitable binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may swell, crack, or disintegrate in storage, while those that contain too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) should be used to form solid oral dosage forms of the invention. The amount of disintegrant used varies based upon the type of formulation and mode of administration, and is readily discernible to those of ordinary skill in the art. Typical pharmaceutical compositions comprise from about 0.5 to about weight percent of disintegrant, preferably from about 1 to about 5 weight percent of disintegrant.

Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md., a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

This invention further encompasses lactose-free pharmaceutical compositions and dosage forms, wherein such compositions preferably contain little, if any, lactose or other mono- or di-saccharides. As used herein, the term "lactose-free" means that the amount of lactose present, if any, is insufficient to substantially increase the degradation rate of an active ingredient.

Lactose-free compositions of the invention can comprise excipients which are well known in the art and are listed in the USP (XXI)/NF (XVI), which is incorporated herein by reference. In general, lactose-free compositions comprise a pharmaceutically acceptable salt of topiramate (e.g., topiramate sodium), a binder/filler, and a lubricant in pharmaceutically compatible and pharmaceutically acceptable amounts. Preferred lactose-free dosage forms comprise a pharmaceutically acceptable salt of topiramate, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, *Drug Stability: Principles & Practice*, 379–80 ($2^{nd}$ ed., Marcel Dekker, NY, N.Y.: 1995). Water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

4.2.2. Controlled and Delayed Release Dosage Forms

Pharmaceutically acceptable salts of topiramate can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, *Controlled Release Dosage Form Design*, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the topiramate salts and compositions of the invention. Examples include, but are not limited to, those described in U.S. Pat. Nos.: 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of topiramate and thus effect controlled delivery of the drug. Examples of specific anion exchangers include, but are not limited to, Duolite® A568 and Duolite® AP143 (Rohm&Haas, Spring House, Pa. USA).

One embodiment of the invention encompasses a unit dosage form which comprises a pharmaceutically acceptable salt of topiramate (e.g., a sodium, potassium, or lithium salt), or a polymorph, solvate, hydrate, dehydrate, co-crystal, anhydrous, or amorphous form thereof, and one or more pharmaceutically acceptable excipients or diluents, wherein the pharmaceutical composition or dosage form is formulated for controlled-release. Specific dosage forms utilize an osmotic drug delivery system.

A particular and well-known osmotic drug delivery system is referred to as OROS® (Alza Corporation, Mountain View, Calif. USA). This technology can readily be adapted for the delivery of compounds and compositions of the invention. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds and compositions of the invention include, but are not limited to, the OROS® Push-Pull™, Delayed Push-Pull™, Multi-Layer Push-Pull™, and Push-Stick™ Systems, all of which are well known. See, e.g., http://www.alza.com. Additional OROS® systems that can be used for the controlled oral delivery of compounds and compositions of the invention include OROS®-CT and L-OROS®. Id.; see also, *Delivery Times*, vol. II, issue II (Alza Corporation).

Conventional OROS® oral dosage forms are made by compressing a drug powder (e.g., topiramate salt) into a hard tablet, coating the tablet with cellulose derivatives to form a semi-permeable membrane, and then drilling an orifice in the coating (e.g., with a laser). Kim, Chemg-ju, *Controlled Release Dosage Form Design*, 231–238 (Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS® drug delivery systems cannot be used to effectively delivery drugs with low water solubility. Id. at 234. Because topiramate salts and complexes of this invention (e.g., topiramate sodium) are far more soluble in water than topiramate itself, they are well suited for osmotic-based delivery to patients. This invention does, however, encompass the incorporation of topiramate, and non-salt isomers and isomeric mixtures thereof, into OROS® dosage forms.

A specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent the exit orifice and in direct or indirect contacting relationship with the expandable layer; and a flow-promoting layer interposed between the inner surface of the wall and at least the external surface of the drug layer located within the cavity, wherein the drug layer comprises a salt of topiramate, or a polymorph, solvate, hydrate, dehydrate, co-crystal, anhydrous, or amorphous form thereof. See U.S. Pat. No. 6,368,626, the entirety of which is incorporated herein by reference.

Another specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a salt of topiramate, or a polymorph, solvate, hydrate, dehydrate, co-crystal, anhydrous, or amorphous form thereof. See U.S. Pat. No. 6,342,249, the entirety of which is incorporated herein by reference.

4.2.3. Parenteral Dosage Forms

Parenteral dosage forms can be administered to patients by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of the invention are well known to those skilled in the art. Examples include, without limitation: sterile water; Water for Injection USP; saline solution; glucose solution; aqueous vehicles such as but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Compounds that alter or modify the solubility of a pharmaceutically acceptable salt of topiramate disclosed herein can also be incorporated into the parenteral dosage forms of the invention, including conventional and controlled-release parenteral dosage forms.

4.2.4. Topical, Transdermal and Mucosal Dosage Forms

Topical dosage forms of the invention include, but are not limited to, creams, lotions, ointments, gels, shampoos, sprays, aerosols, solutions, emulsions, and other forms know to one of skill in the art. See, e.g., *Remington's Pharmaceutical Sciences*, 18$^{th}$ ed., Mack Publishing, Easton, Pa. (1990); and *Introduction to Pharmaceutical Dosage Forms*, 4$^{th}$ ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., *Remington's Pharmaceutical Sciences*, 18$^{th}$ Ed., Mack Publishing, Easton, Pa. (1990).

Transdermal and mucosal dosage forms of the invention include, but are not limited to, ophthalmic solutions, patches, sprays, aerosols, creams, lotions, suppositories, ointments, gels, solutions, emulsions, suspensions, or other forms known to one of skill in the art. See, e.g., *Remington's Pharmaceutical Sciences*, 18$^{th}$ Ed., Mack Publishing, Easton, Pa. (1990); and *Introduction to Pharmaceutical Dosage Forms*, 4$^{th}$ Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer the active ingredient(s) of the invention include, but are not limited to, those disclosed in U.S. Pat. Nos.: 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466;465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference.

Suitable excipients (e.g., carriers and diluents) and other materials that can be used to provide transdermal and mucosal dosage forms encompassed by this invention are well known to those skilled in the pharmaceutical arts, and depend on the particular tissue or organ to which a given pharmaceutical composition or dosage form will be applied. With that fact in mind, typical excipients include, but are not limited to water, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with pharmaceutically acceptable salts of topiramate of the invention. For example, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, dehydrates, co-crystals, solvates, polymorphs, anhydrous, or amorphous forms of the pharmaceutically acceptable salt of topiramate can be used to further adjust the properties of the resulting composition.

4.2.5. Kits

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a unit dosage form of a pharmaceutically acceptable salt of topiramate and a unit dosage form of a second pharmacologically active compound, such as caffeine, anticonvulsants, or antiepileptics. Preferably, the pharmaceutically acceptable salt of topiramate is topiramate sodium, topiramate lithium, or topiramate potassium, or a polymorph, solvate, hydrate, dehydrate, co-crystal, anhydrous, or amorphous form thereof. More preferably, the pharmaceutically acceptable salt of topiramate is topiramate sodium, or a polymorph, solvate, hydrate, dehydrate, co-crystal, anhydrous, or amorphous form thereof. A kit may further comprise a device that can be used to administer the active ingredient. Examples of such devices include, but are not limited to, syringes, drip bags, patches, and inhalers.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

The invention is further defined by reference to the following examples. It will be apparent to those skilled in the art that many modifications, both to materials and methods, can be practiced without departing from the scope of this invention.

5. EXAMPLES

Certain embodiments of the invention, as well as certain novel and unexpected advantages of the invention, are illustrated by the following non-limiting examples.

5.1. Example 1

Synthesis and Analysis of Topiramate Sodium Trihydrate 5.1.1. Synthesis of Topiramate Sodium Trihydrate 0.50 g of topiramate (Cheminor Drugs Ltd., Hyderabad, India, Batch No. TP001J00) was suspended in 10 mL of distilled water in a scintillation vial. 1.4 mL of 1 N NaOH (VWR, West Chester, Pa.) was added to dissolve the drug with heating. A TEFLON-coated magnetic stirbar and hotplate-stirrer were used to bring the compound into solution, after which the warm solution was filtered through a #1 filter paper (Whatman) into a clean beaker containing a dry TEFLON-coated stirbar. The beaker was then heated with stirring to reduce the volume of the solution to the point of super saturation. The beaker was stored at room temperature, lightly capped to allow for slow evaporation. After 3 days, small block-like crystals were observed by optical microscopy at 100-fold magnification. On the fourth day, two large crystals were seen which had the approximate dimensions of 0.5 cm×0.5 cm×0.2 cm. The resulting product was a clear colorless birefringent crystalline substance. The crystals are square plates with angled sides. The crystals lose waters of hydration above 50° C., decomposes above ~150° C. Alternatively, storage under low humidity conditions (close to zero percent, controlled by the presence of phosphorous pentoxide) removes the water of hydration from the crystals even at room temperature.

Thermal microscopy indicates more than one polymorph, or hydration state, exists. In this analysis, a small crystallite was cleaved from a large crystal of topiramate sodium trihydrate prepared in this example. The crystal extinguished on the polarizing microscope when the crystal edges were aligned with the polarizer and analyzer. Conoscopy showed that the crystals were biaxial. The crystallite was loaded into a glass crucible and covered with the crucible's glass cover, and then placed into a FP900 Hotstage microscope (Mettler Toledo). The sample was heated from 30° C. to 180° C. at 10° C./minute, in 5° C. increments. Between 80° C. and 85° C., the birefringence annealed out of the crystal leaving an amorphous gel-like mass with similar shape to the original crystal. A free flowing liquid was not observed at this time. At 110° C. new crystals, rectangular birefringent blades, grew within the gel-like mass. The new crystals extinguished when the crystal edges were aligned with the polarizer and analyzer. At 120° C. other crystals grew in. These crystals extinguished when the crystal edges were not aligned with the polarizer and analyzer. At 160° C. the birefringence anneals out of the crystals formed at 110° C., then between 170° C. and 175° C. all of the crystals melted. No crystals formed upon cooling the resulting melted material to room temperature. The combined observations demonstrate the presence of two polymorphs in addition to the as-made sodium salt trihydrate.

A sample of the compound prepared above was then examined by powder X-ray diffraction (PXRD), thermogravimetric analysis (TGA), and differential scanning calorimetry (DSC), as set forth below.

5.1.2. Analysis by PXRD, DSC, and TGA

A powder X-ray diffraction pattern for the salt sample prepared in this example was performed using a D/Max Rapid diffractometer (Rigaku/MSC, The Woodlands, Tex., U.S.A.), which uses as its control software RINT Rapid Control Software, Rigaku Rapid/XRD, version 1.0.0 (©1999 Rigaku Co.). In addition, the analysis software used were RINT Rapid display software, version 1.18 (Rigaku/MSC), and JADE XRD Pattern Processing, versions 5.0 and 6.0 (©1995–2002, Materials Data, Inc.).

For the PXRD analysis, the acquisition parameters were as follows: source wasCu/$K_\alpha$1.5406 Å; x-y stage was manual; collimator size was 0.3 mm; capillary (Charles Supper Company, Natick, Mass., U.S.A.) was 0.3 mm; reflection mode was used; the power to the X-ray tube was 46 kV; the current to the X-ray tube was 40 mA; the omega-axis was oscillating in a range of 0–5 degrees at a speed of 1 degree/minute; the phi-axis was spinning at an angle of 360 degrees at a speed of 2 degrees/second; 0.3 mm collimator; the collection time was 60 minutes; the temperature was room temperature; and the heater was not used. The sample was presented to the X-ray source in a quartz capillary.

In addition, the analysis parameters were as follows: the integration 2-theta range was 2–60 degrees; the integration chi range was 0–360 degrees; the number of chi segments was 1; the step size used was 0.02; the integration utility was cylint; normalization was used; dark counts was 8; omega offset was 180; and chi and phi offsets were 0.

Figure 1:
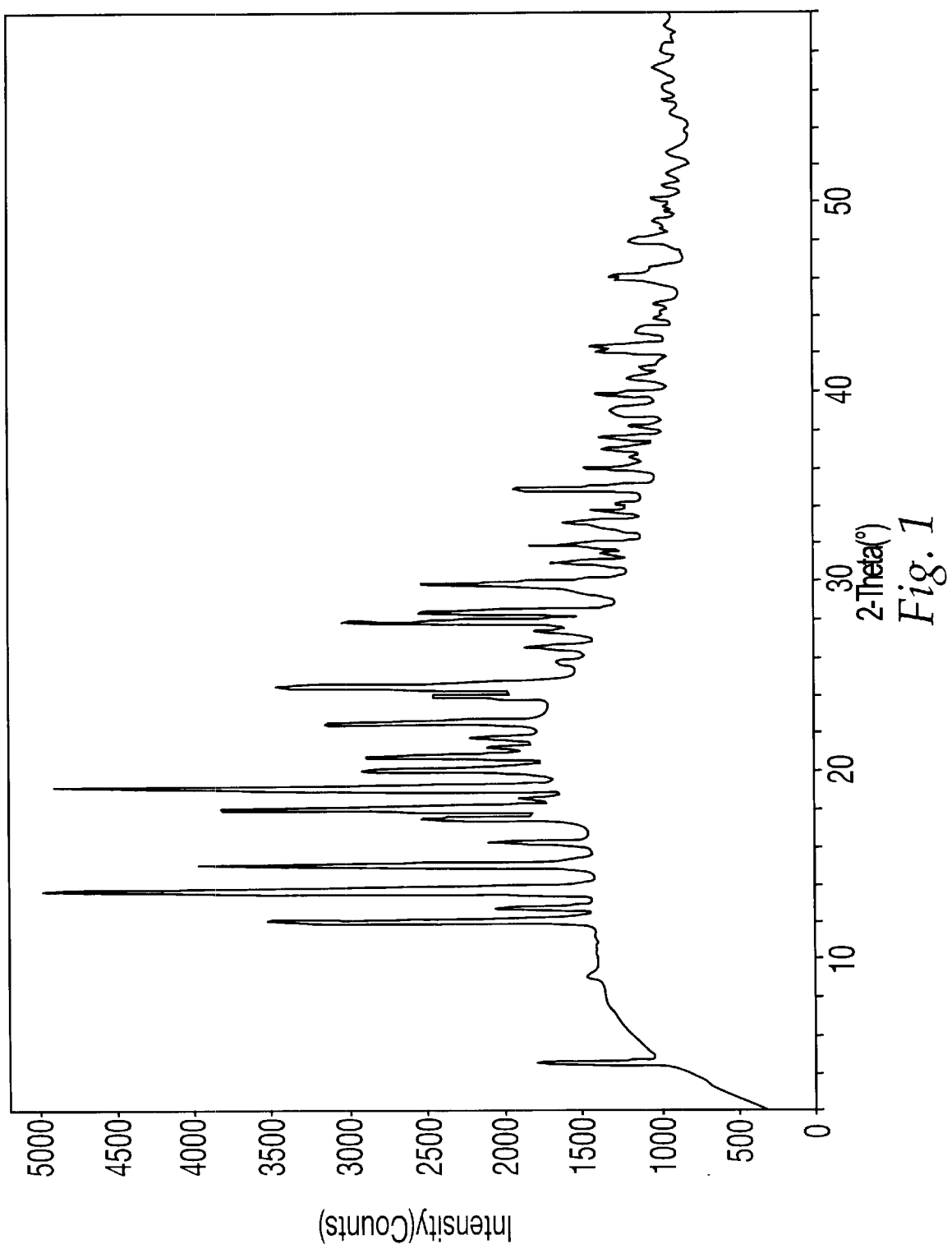

The PXRD pattern for the resulting compound (topiramate sodium trihydrate) is shown in FIG. 1. In the diffractogram of FIG. 1, the background has not been removed.

DSC analysis of the salt sample prepared in this example was performed using a Q1000 Differential Scanning Calorimeter (TA Instruments, New Castle, Del., U.S.A.), which uses Advantage for QW-Series, version 1.0.0.78, Thermal Advantage Release 2.0 (©2001 TA Instruments-Water LLC). In addition, the analysis software used was Universal Analysis 2000 for Windows 95/95/2000/NT, version 3.1E;Build 3.1.0.40 (©2001 TA Instruments-Water LLC).

For the DSC analysis, the purge gas used was dry nitrogen, the reference material was an empty aluminum pan that was crimped, and the sample purge was 50 mL/minute.

Figure 2:
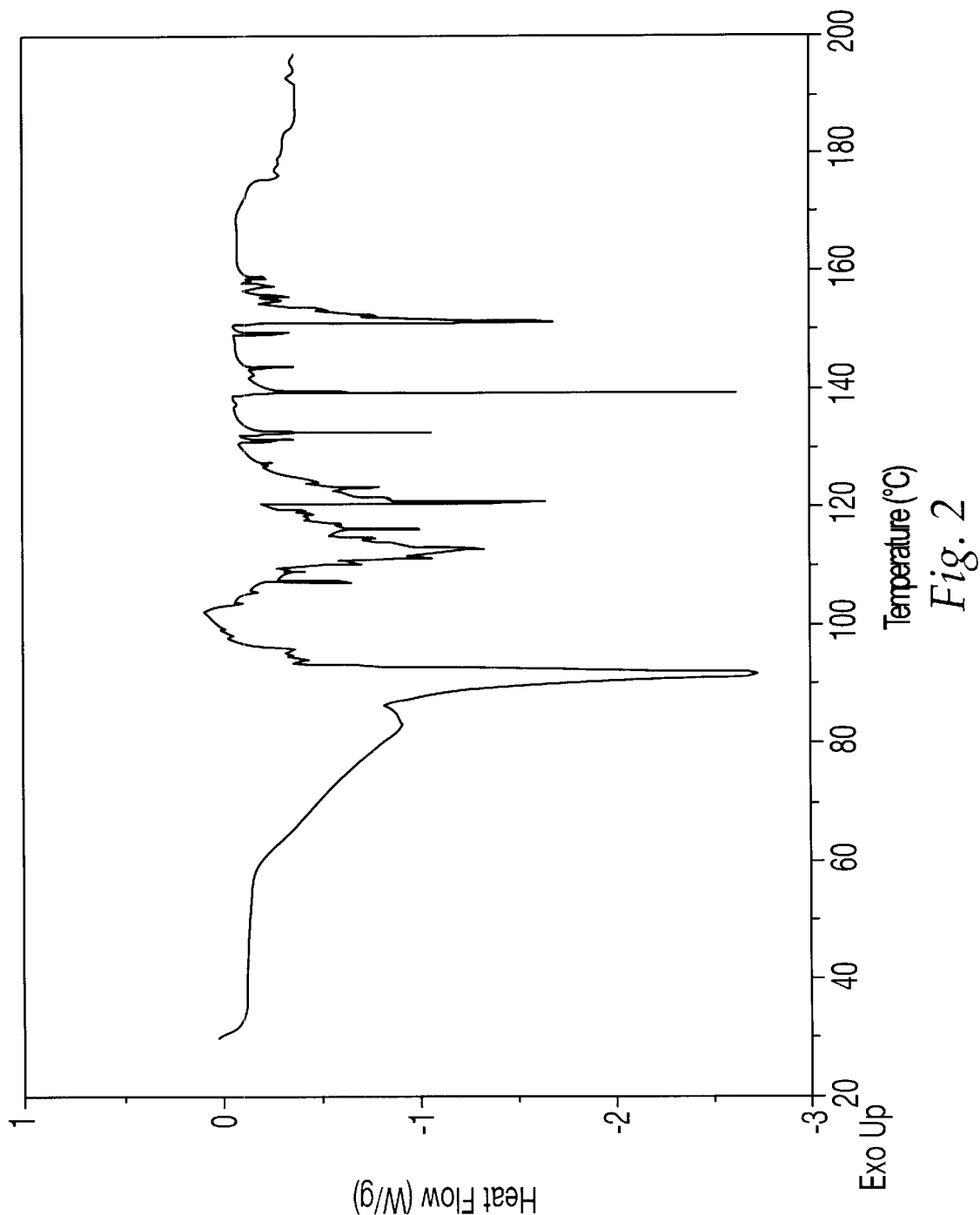

DSC analysis of the sample was performed by placing 3.230 mg of sample in an aluminum pan with a crimped pan closure. The starting temperature was 20° C. with a heating rate of 10° C./minute, and the ending temperature was 200° C. The resulting DSC analysis is shown in FIG. 2.

TGA analysis of the salt sample prepared in this example was performed using a Q500 Thermogravimetric Analyzer (TA Instruments, New Castle, Del.;, U.S.A.), which uses Advantage for QW-Series, version 1.0.0.78, Thermal Advantage Release 2.0 (©2001 TA Instruments-Water LLC). In addition, the analysis software used was Universal Analysis 2000 for Windows 95/95/2000/NT, version 3.1E;Build 3.1.0.40 (©2001 TA Instruments-Water LLC).

For all of the TGA experiments, the purge gas used was dry nitrogen, the balance purge was 40 mL/minute $N_2$, and the sample purge was 60 mL/minute $N_2$.

Figure 3:
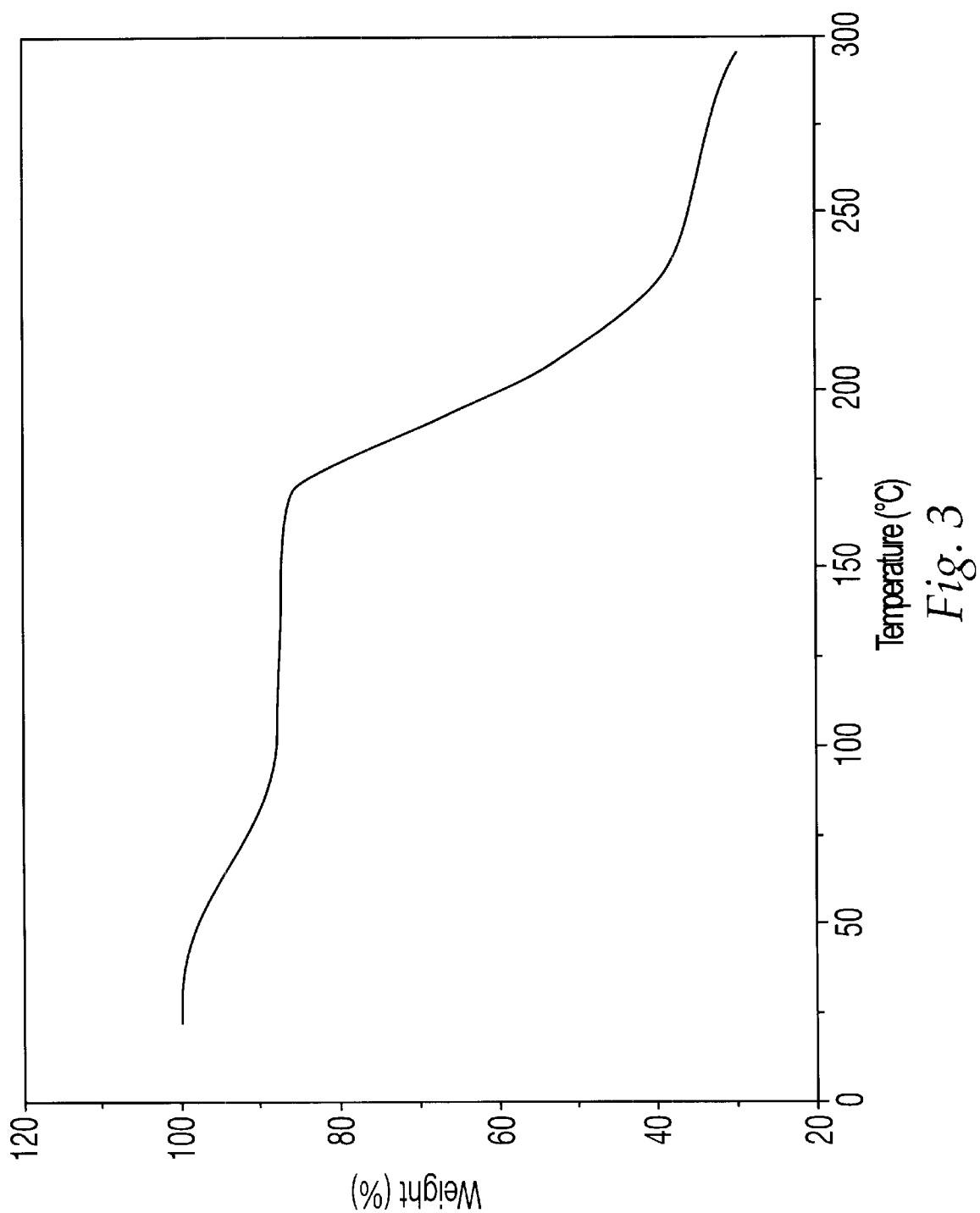

TGA of the sample from this example was obtained by weighing 4.159 mg of sample in a platinum pan and placing it in the analyzer. The starting temperature was 20° C. with a heating rate of 10° C./minute, and the ending temperature was 300° C. The resulting TGA analysis is shown in FIG. 3.

Sample crystals from this example were submitted to single-crystal X-ray analysis: Nonius Kappa CCD diffractometer, Mo ($K_\alpha$) radiation ($\lambda$=0.71073 Å), Collect data collection software (Nonius 1998), Denzo data reduction software (Z. Otinowski and W. Minor 1996), cell refinement carried out using HKL Scalepack (Z. Otwinowski and W. Minor, 1997), structure solution using SIR92 (A. Altomare, G. Cascarano, C. Giacovazzo, M. C. Burla, G. Polidori, M. Camali, 1994), structure refinement using SHELXL-97 (G. M. Scheldrick, 1997). The structure parameters are shown in Table 1. The combined data show that topiramate sodium trihydrate, distinct from topiramate, was prepared.

TABLE 1

Single Crystals X-Ray Structure Data

| | | | |
|---|---|---|---|
| Empirical formula | $C_{12}H_{26}NNaO_{11}S$ | Reflections for indexing | 771 |
| Formula weight | 415.39 g/mol | Theta ranged for data collection | 3.44 to 23.24 deg |
| Temperature | 293 (3) K | Index ranges | $-7 <= h <= 7$, $-8 <= k <= 8$, $-42 <= l <= 43$ |
| Wavelength | 0.71072 Å | Reflections collected/unique | 2543/2543 [R(int) = 0.062] |
| Crystal description/color | Block/clear | Completeness to theta = 23.34 | 96.6% |
| Crystal system, space group | Orthorhombic, $P2_12_12_1$ | Absorption correction | Numeric |
| Unit cell dimensions | A = 6.6060 (2) Å alpha = 90 deg b = 7.4490 (2) Å beta = 90 deg c = 39.1170(12) Å gamma = 90 deg | Max. and min. transmission | 0.9481 and 0.9062 |
| Volume | 1924.87 (10) $Å^3$ | Refinement method | Full-matrix least-squares on $F^2$ |
| Z, calculated density | 4, 1.433 $Mg/m^3$ | Data/restraints/parameters | 2543/13/255 |
| Absorption coefficient | 0.245 $mm^{-1}$ | Goodness-of-fit on $F^2$ S = root(sum(w*D*D)/(n-p)) where D = (Fo*Fc – Fc*Fc) | 1.003 |
| F(000) | 880 | Final R indices [I > 2sigma(I)] | R1 = 0.0488, wR2 0.1172 |
| Crystal size | 0.41 × 0.34 × 0.22 mm | R indicies (all data) R1 = sum\|\|Fo\|-\|Fc\|\|/sum\|Fo\|, wR2 = root (sum(w*D*D)/sum(w*Fo*Fo)) where D = Fo*Fo – Fc*Fc Weighting scheme Calc w = 1/[$s^{2\wedge}$($Fo^2$) + (0.0811P)$^\wedge$2 + 0.0000P where P = ($Fo^2$ + $2Fc^2$)/3 | R1 = 0.0666, wR2 0.1267 |
| Absolute structure parameter | 0.84 (14) | Largest difference peak and hole | 0.228 and –0.220 e.$Å^{-3}$ |

5.2. Example 2

A Second Synthesis and Analysis of Topiramate Sodium Trihydrate

5.2.1. Synthesis of Topiramate Sodium Trihydrate 10.09 g (29.73 mmoles) of topiramate (Cheminor Drugs Ltd., Hyderabad, India, Batch TP001J00) was placed in a 250 mL beaker and 100.0 mL of HPLC grade water (J T Baker, Phillipsburg, N.J. USA, Lot V32E17) was added. 1.36 g (34.0 mmoles) of sodium hydroxide (Sigma, St. Louis, Mo. USA, Lot 99H0120) was added and the mixture was stirred with a TEFLON® coated magnetic stir bar using a hot plate/stir plate. The mixture was heated to 60° C. to dissolve. The solution was filtered and evaporated at 60° C. while blowing air over the surface using a TYGON tube attached to an air source to reduce the volume to 15 mL, and the flask was placed in a cold room (4° C.) overnight.

Crystals grew overnight. The mixture was filtered and dried to yield 305 mg topiramate sodium as large, block-like crystals. Elemental analysis: calc. C, 34.70; H, 6.31; N 3.37%; found C, 34.90; H, 6.04; N 3.36%. mp 80–85° C., recrystallization from melted material 110–120° C., second mp 170–175° C. PXRD Cu-K$_\alpha$ radiation (1.5406 Å) first 8 peaks (peak number/2$\Theta$ value), #1/4.51°, #2/12.09°, #3/12.709°, #4/13.67°, #5/15.01°, #6/16.17°, #7/17.19°, #8/17.55°. The pH of a 400 mg/mL solution of the compound in distilled water was about 11.2, which was determined using a Thermo Orion pH meter, Model 525A+ (Orion Research, Inc., Beverly, Mass. USA).

5.2.2. Analysis by PXRD and Raman

Raman spectroscopy of a sample from this example was performed using a Nicolet Almega Dispersive Raman Spectrometer/Microscope, controlled by Omnic software v. 5.2a. Spectra ranges were 3250 to 105 cm$^{-1}$, using 10 $\mu$m pinhole aperture, and ten consecutive 2-second exposures. The resulting spectra were displayed using Omnic software v. 5.2a.

Figure 4:
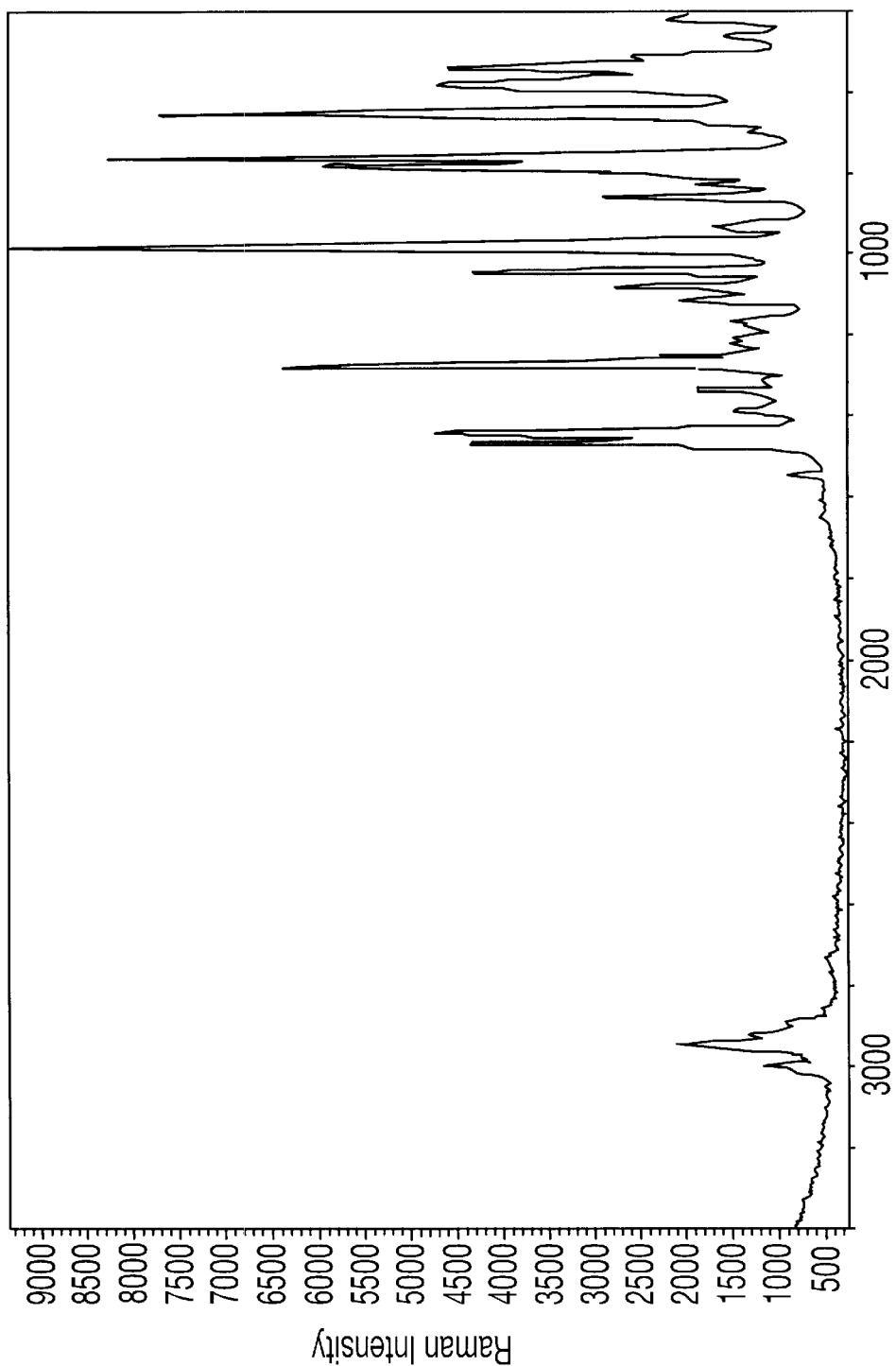

The resulting Raman spectrum is shown in FIG. 4, which shows the characteristic shifts for —SO$_2$—NR$_2$ were observed at 1380, 1162 and 529 cm$^{-1}$.

Figure 5:
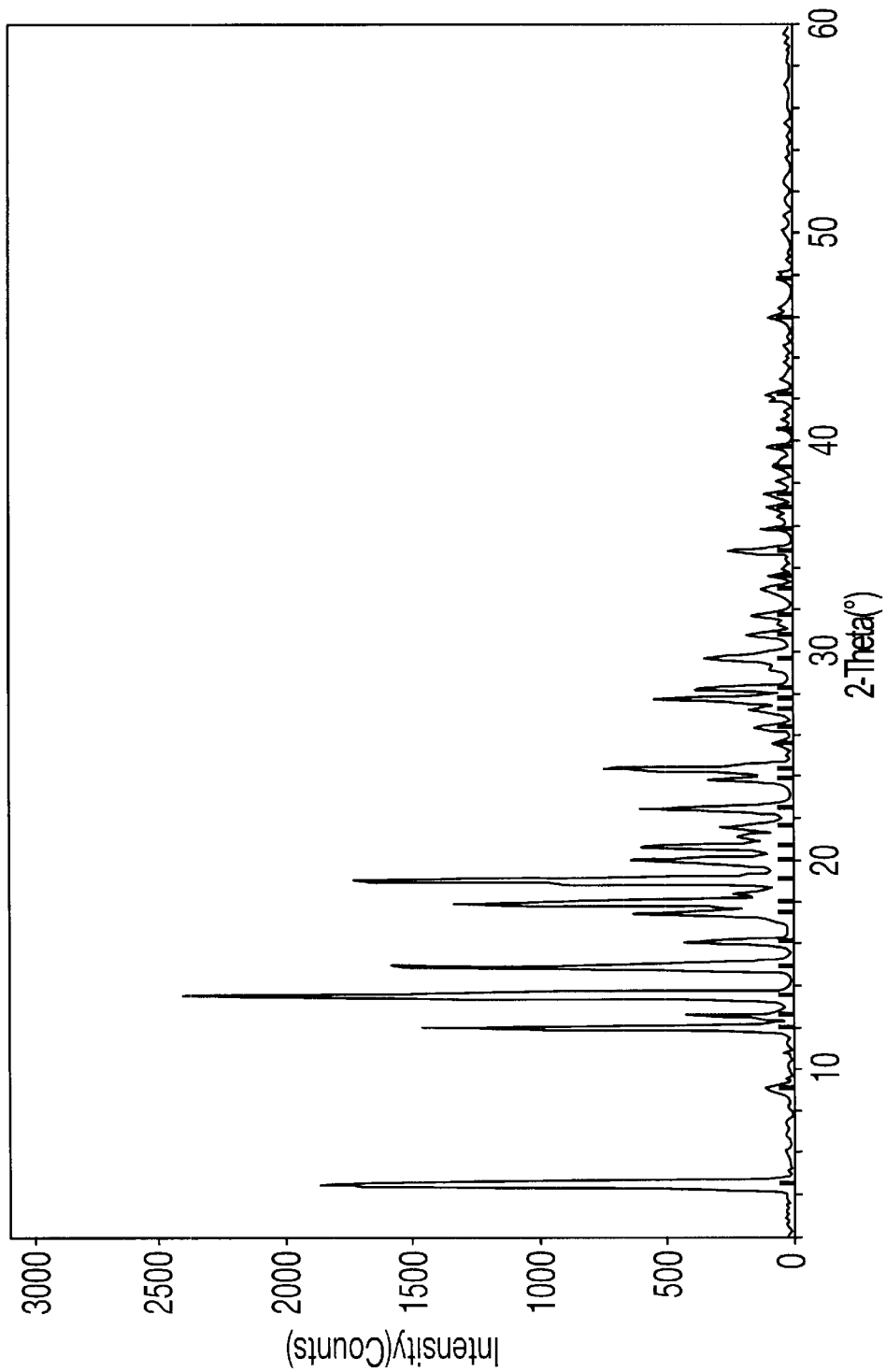
FIG. 5 shows the powder X-ray diffraction pattern of the compound synthesized in Example 2.

A powder X-ray diffraction pattern for the salt sample prepared in this example was performed using a the same methods and equipment described in this example. The PXRD pattern for the resulting compound (topiramate sodium trihydrate) is shown in FIG. 5.

These data indicate that topiramate sodium trihydrate, distinct from topiramate, was prepared.

5.2.3. Estimation of Solubility

The solubility of the topiramate sodium trihydrate prepared in this example in water, ethanol, methanol, and THF was estimated by determining the minimum amount of solvent necessary to dissolve a known amount of the compound. In general, a predetermined amount of the compound was placed in a small glass vial, and then solvent was added drop-wise at room temperature until no visible solid remained in the vial. The specific details of each experiment are set forth in Table I below:

TABLE 2

SOLUBILITY ESTIMATION

| Solvent | Weight of topiramate sodium trihydrate | Amount of Solvent | Solubility (amount of solid in mL of solvent) | Average Solubility |
|---|---|---|---|---|
| Water: | | | | |
| Trial 1 | 28.7 mg | 20 $\mu$L | 1.435 g/mL | 1.33 g/mL |
| Trial 2 | 24.7 mg | 20 $\mu$L | 1.235 g/mL | |
| Ethanol: | 18.8 mg | 50 $\mu$L | 376 mg/mL | |
| THF | 10.6 mg | 240 $\mu$L | 44.2 mg/mL (slight overestimate) | |
| Methanol: | | | | |
| Trial 1 | 44.7 mg | 35 $\mu$L | 1.28 g/mL | 1.47 g/mL |
| Trial 2 | 48.1 mg | 30 $\mu$L | 1.60 g/mL | |
| Trial 3 | 38.3 mg | 25 $\mu$L | 1.53 g/mL | |

These data indicate that the pharmaceutically acceptable salts of topiramate, such as topiramate sodium, of the invention offer increased solubility, which allows the pharmaceutically acceptable salts of the invention to be formulated in various desirable routes, such as a low volume injectable, rapid oral dissolve or a controlled- or extended release dosage form.

Figure 6:
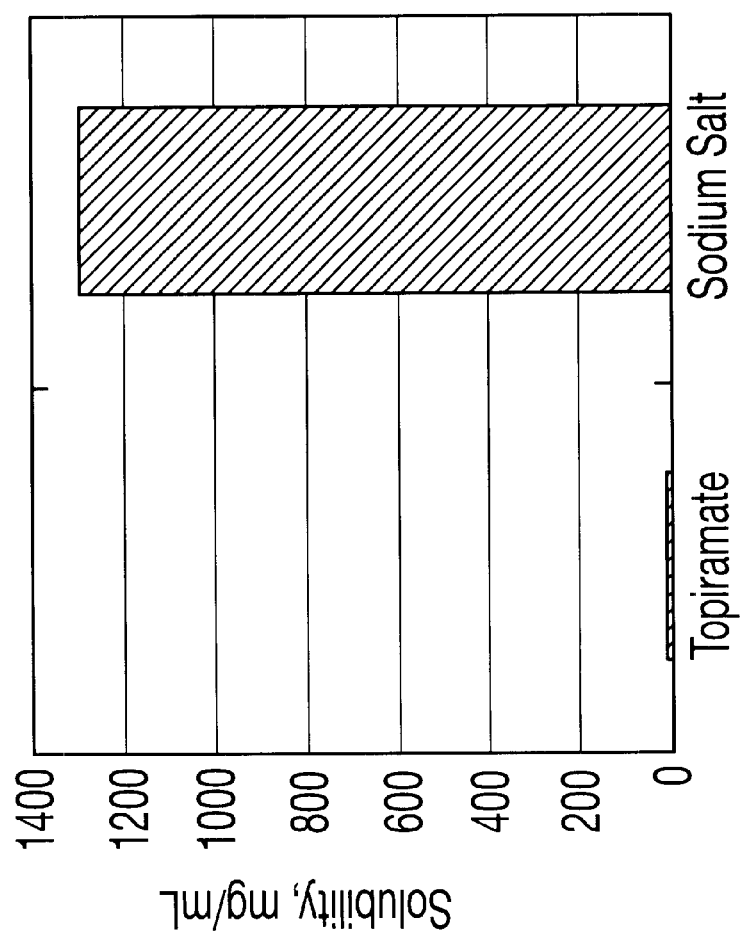
FIG. 6 shows the aqueous solubility of topirimate sodium trihydrate as compared to that of topiramate.
Figure 7:
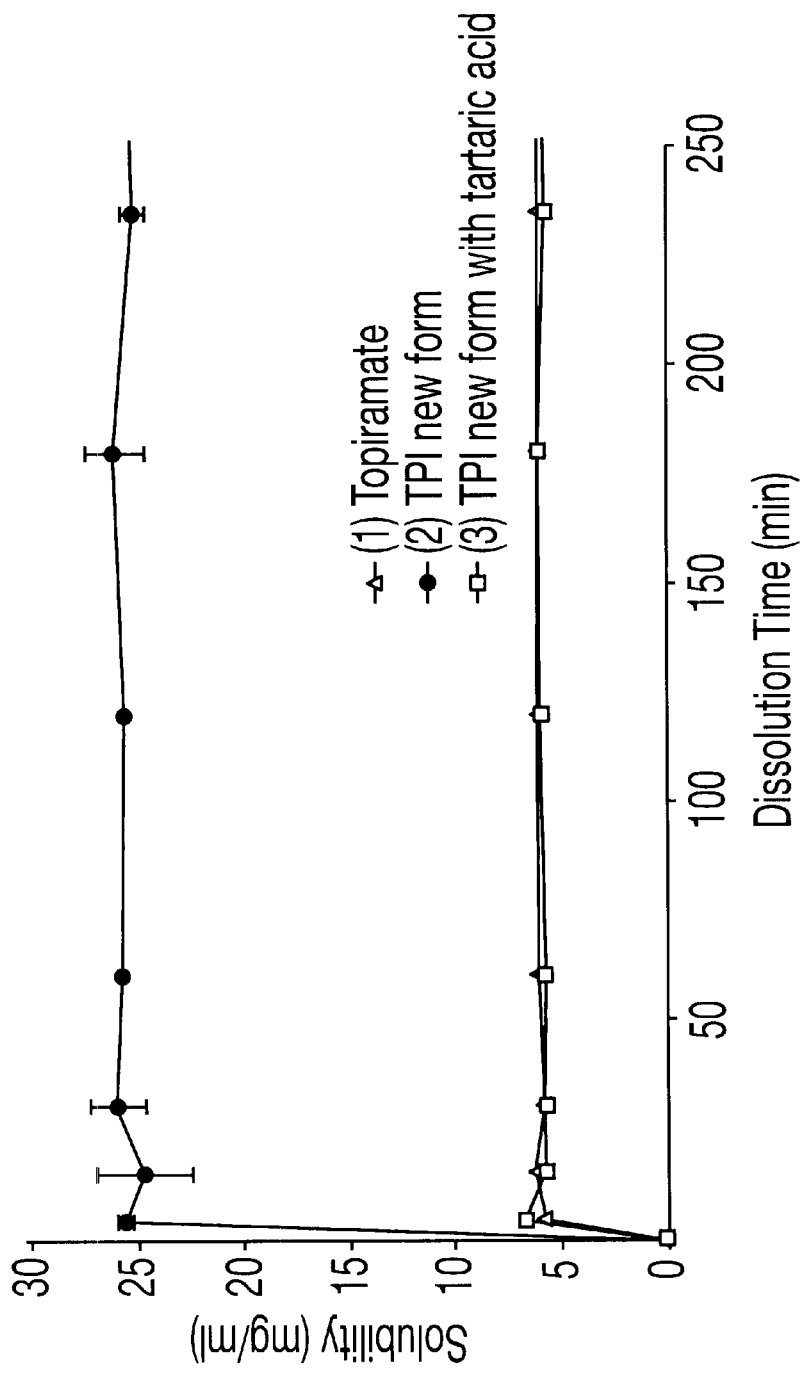
FIG. 7 shows the dissolution curves in 0.01 N HCl of (1) topiramate crystals, (2) topiramate sodium trihydrate, and (3) topiramate sodium trihydrate dry mixed with 1.1 equivalents of tartaric acid.

FIG. 6 provides results of a comparison between the aqueous solubility of topirimate sodium trihydrate with that of topiramate. The sodium salt was found to be over 100 times more soluble at 1.3 g/mL vs. the literature value of 9.8 mg/mL. Independently, a set of dissolution curves were obtained in 0.01 N HCl (representative of a modestly acidic stomach), and these are shown in FIG. 7. Three preparations were tested: (1) topiramate crystal form (Reddy Cheminor), (2) topiramate sodium salt trihydrate and (3) topiramate sodium salt trihydrate dry mixed with 1.1 equivalents of tartaric acid. Dissolution was found to be rapid with all forms, and was essentially complete in 5 minutes. Relative to (1) and (3), sample (2) showed increased solubility at the equilibrium condition, with an associated pH of 9.5. The nominal concentration of drug in each case was about 110 mM (37 mg/mL free acid concentration) and hence (1) and (3) remained as suspensions while (2) was not saturated at the end of the experiment.

5.3. Example 3

A Third Synthesis and Analysis of Topiramate Sodium Trihydrate 5.3.1 Synthesis of Topiramate Sodium Trihydrate 0.97 g (2.9 mmols) of topiramate (Cheminor Ltd.), 10 mL distilled water, and 2.8 mL 1N NaOH (2.8 mmol) were added to a glass beaker, warmed on a hotplate to 60° C. and stirred with a TEFLON-coated stir bar on a magnetic stirplate. The solid topiramate dissolved in about 25 minutes. The solution was filtered through a #4 filter paper and transferred into a clean vial with a TEFLON-coated stir bar. The solution was concentrated by evaporation until solid formed. The mixture was dried further by blowing air over the vial. The dried solid was dissolved in 5 mL of 2% water (v/v) in ethanol. The solution was concentrated and cooled in a refrigerator at 4° C. overnight. Fine white crystals formed and were filtered, dried, and weighed (0.85 g, 88%).

5.3.2. Analysis by TGA and PXRD

A sample of the compound prepared above was then examined by TGA and PXRD using the same procedures and equipment described in Example 1.

TGA of a sample from this example was observed by weighing 3.0630 mg of sample in a platinum pan and placing it in the analyzer. The starting temperature was 20° C. with a heating rate of 10° C./minute, and the ending temperature was 190° C. The resulting TGA analysis is shown in FIG. 8. Mass losses of 13% and 39% at 41° C. and 174° C., respectively, were observed by TGA.

A sample of the compound prepared in this example was examined by PXRD using a collection time of 10 minutes. The PXRD pattern for the resulting compound (topiramate sodium trihydrate) is shown in FIG. 9. A PXRD pattern for topiramate sodium trihydrate includes the identifying features listed below in Table 2:

TABLE 3

Topiramate Sodium Trihydrate

| 2-theta | Intensity |
|---|---|
| 4.51 ± 0.05 | Medium |
| 13.65 ± 0.05 | Strong |
| 19.15 ± 0.05 | Medium |

These data show that topiramate sodium trihydrate, distinct from topiramate, was prepared.

5.3.3. Physical Stability

The physical stability of the topiramate sodium trihydrate prepared in this example was initially evaluated by TGA, which demonstrated that the hydrate stays intact up to and including 40° C. A further study on physical stability of a sample from this example was conducted in glass vials at preset temperatures and controlled relative humidities. The humidities stored at room temperature were controlled using saturated salt solutions (see H. Nyquist, *Pharm. Tech.* 4(2):47–48 (1983)). At other temperatures, the oven configurations allowed humidity control. After 2 weeks, samples at various conditions were tested by TGA and PXRD to assess whether the crystalline topiramate sodium trihydrate remained intact or not. The data in Table 3 summarize findings after 2 weeks of incubation.

TABLE 4

Physical Stability Study After 2 Weeks

| Temp (° C.) | % Relative Humidity | Result |
| --- | --- | --- |
| 5 | Ambient (refrigerated) | Trihydrate |
| 25 | <5 | Trihydrate & some amorphous |
| 25 | 31 | Trihydrate |
| 25 | 75 | Trihydrate |
| 40 | Ambient (<20) | Trihydrate |
| 40 | 75 | Trihydrate |
| 60 | Ambient (<10) | Amorphous |
| 80 | Ambient (<5) | Amorphous |

These data further support the physical stability of the topiramate sodium trihydrate over a range of temperatures up to and including 40° C., as well as relative humidities from about 5% up to and including 75%. No chemical degradation is observed by HPLC analysis in samples stored for 2 weeks at 25° C./<5% relative humidity (RH), 25° C./31% RH, 25° C./75% RH, 40° C./ambient RH, or 40° C./75% RH. No chemical degradation is observed by HPLC analysis in samples stored for >12 weeks at 25° C./<5% RH, 25° C./31% RH, 25° C./75% RH, 40° C./75% RH. Degradates were observed by HPLC when material was stored at or above 60° C. for at least 2 weeks.

5.4. Example 4

IN VIVO Characteristics of Topiramate Sodium Trihydrate

The bioavailability of topiramate provided by (1) TOPAMAX® was compared to that of topiramate provided by (2) topiramate sodium trihydrate and a (3) combination of topiramate sodium trihydrate dry mixed with 1.1 equivalents of tartaric acid using male Sprague-Dawley rats dosed with oral gavage of size 9 gelatin capsules (Torpac, Fairfield, N.J.). The capsules contained an amount of solid powder sufficient to provide a dose equivalent to 30 mg/kg (mpk) of free topiramate (corrected for any counterion, hydrate and tartaric acid constituent). Plasma samples were analyzed by LC/MS/MS using a method based on a human plasma assay of topiramate. Tests were conducted by MDS Pharma Services (Montreal, Canada).

The in vivo data yielded by these tests are shown in FIG. 10. The crystalline salt in (2) has a very fast onset time, with the peak of plasma concentration being observed at the first time point of 0.5 h. A statistical difference (p=0.01) was found between the time to peak plasma levels ($t_{max}$) of (2) vs. (1) and (3). The data for (2) are comparable to an oral solution of TOPAMAX®. The neutralized formulation (3) behaves similarly to (1), and no statistical difference was seen between their $t_{max}$ values (p=0.38).

The comparison between (1) and (3) illustrates the possibility of modulating the rate of absorption of the sodium salt by changing formulation in the solid oral dosage form. On the other hand, the fast absorption of the sodium salt in the absence of acidifying agent suggests its usefulness in immediate release formulations for the treatment of pain, emerging convulsion episodes, or other conditions. The sodium salt may further be used in controlled release dosage forms that require higher solubility and greater intrinsic osmolality than is provided by topiramate itself.

5.5. Example 5

Synthesis and Analysis of Topiramate Lithium

5.5.1 Synthesis of Topiramate Lithium

A 20 mL scintillation vial was loaded with 528.6 mg (1.558 mmols) of topiramate (Cheminor Drugs Ltd., Hyderabad, India, Batch TP001.J00) and 10 mL HPLC grade water (J. T. Baker, Phillipsburg, N.J. USA, Lot V32E17). 71.4 mg (1.702 mmols) of solid LiOH monohydrate (Aldrich, St. Louis, Mo. USA, 99.95%, Lot 00331KI) was mixed in the topiramate/water solution using a TEFLON-coated stirring bar. The solution was heated on a hotplate to dissolve, filtered through a 0.2 μm GELMAN ACRODISK filter (Pall Life Sciences, Ann Arbor, Mich. USA). The solution was concentrated to about 5 mL and placed in the refrigerator at about 4–8° C. overnight. A clear oil was left. Further evaporation in a vacuum oven at 55° C. under vacuum for about 1–2 hours yielded an amorphous white powdery solid.

5.5.2 Analysis by DSC and TGA

A sample of the compound prepared above was then examined by thermogravimetric analysis (TGA) and differential scanning calorimetry (DSC), using the same procedures and equipment described in Example 1.

TGA of the sample from this example was observed by weighing 3.2880 mg of sample in a platinum pan and placing it in the analyzer in dynamic mode. The starting temperature was 20° C. with a heating rate of 50° C./minute, and the ending temperature was 400° C. The resulting TGA analysis is shown in FIG. 11. A mass loss of 3.1% was observed at 149° C. by TGA.

DSC analysis of a sample of the compound synthesized in this example was performed by placing 4.713 mg of sample in an aluminum pan with a crimped pan closure. The starting temperature was 30° C. with a heating rate of 20° C./minute, and the ending temperature was 300° C. The resulting DSC analysis is shown in FIG. 12.

These data show that topiramate lithium, distinct from topiramate, was prepared.

5.6. Example 6

Synthesis and Analysis of Topiramate Potassium

5.6.1. Synthesis of Topiramate Potassium

A 20 mL scintillation vial was loaded with 556.8 mg (1.641 mmols) of topiramate (Cheminor Drugs Ltd., Hyderabad, India, Batch TP001.J00) and 1 mL THF (Sigma, St. Louis, Mo. USA, 99.0+%, Lot 50k1485), and all of the topiramate dissolved. 89.9 mg (1.602 mmols) of solid KOH (Spectrum, Lot PN0690) was dissolved in the topiramate/ THF solution. The solution was allowed to evaporate overnight at room temperature leaving an amorphous solid. The solid was further dried by placing it in a vacuum desiccator 1 white brittle solid.

5.6.2. Analysis by TGA

A sample of the compound prepared above was then examined by TGA using the same procedures and equipment described in Example 1.

TGA of a sample from this example was observed by weighing 6.4900 mg of sample in a platinum pan and placing it in the analyzer and running in dynamic mode. The starting temperature was room temperature with a heating rate of 50° C./minute, and the ending temperature was 400° C. The resulting TGA analysis is shown in FIG. 13. Cumulative mass losses of 2.1%, 2.8% and 2.7% at 85, 132 and 172° C., respectively, were observed by TGA relative to the starting mass in the pan.

These data indicate that topiramate potassium, distinct from topiramate, was prepared.

5.7. Example 7

Synthesis of Topiramate and Caffeine Co-Crystal

Hot stage microscopy experiments were carried out to generate a co-crystal of topiramate and caffeine. Caffeine (anhydrous, 99.0+%, Fluka, Lot 384769) was melted (mp.= 234–236° C.) and recrystallized between a glass slide and a cover slip on a Mettler-Toledo FP950t stage mounted on a Zeiss Axioplan II polarized light microscope. The hotstage was allowed to cool to 30° C. Topiramate (Cheminor Ltd., Batch TP001J00) was then placed on the glass slide in contact with the edge of the cover slip, and was melted (mp.=124–125° C.) and the melt came into contact with the recrystallized caffeine by capillary action. The melted topiramate recrystallized overnight while held at 70° C.

The interfacial region between the pure topiramate and caffeine region was crystalline and had a different morphology than either of the pure phases. The sample was heated slowly and the interfacial region melted between 105° C and 106.5° C.

The absence of multiple melt regions (eutectics) indicated that only one pure topiramate-caffeine co-crystalline phase exists.

While the invention has been described with respect to the particular embodiments, it will be apparent to those skilled in the art that various changes and modifications may be made without departing from the spirit and scope of the invention as defined in the claims. Such modifications are also intended to fall within the scope of the appended claims.

What is claimed is:

1. Topiramate sodium trihydrate.

* * * * *

Disclaimer

6,559,293—Orn Almarsson, Shrewsbury, MA (US); Jules Remenar, Framingham, MA (US); Matthew L. Peterson, Framingham, MA (US). TOPIRAMATE SODIUM TRIHYDRATE. Patent dated May 6, 2003. Disclaimer filed Jan. 9, 2006, by the assignee, Ortho-McNeil Pharmaceutical, Inc.

Hereby enters this disclaimer to claim 1, of said patent.

*Official Gazette, March 21, 2006*